United States Patent

Yee et al.

[11] Patent Number: 5,858,799
[45] Date of Patent: Jan. 12, 1999

[54] SURFACE PLASMON RESONANCE CHEMICAL ELECTRODE

[75] Inventors: Sinclair S. Yee, Seattle; Chuck C. Jung, Lynnwood; Stevan B. Saban, Snohomish; Robert B. Darling, Lake Forest Park, all of Wash.

[73] Assignee: University of Washington, Seattle, Wash.

[21] Appl. No.: 738,445

[22] Filed: Oct. 25, 1996

Related U.S. Application Data

[60] Provisional application No. 60/007,029 Oct. 25, 1995.
[51] Int. Cl.$^6$ .................................................. G01N 21/55
[52] U.S. Cl. ........................... 436/164; 436/73; 436/149; 436/150; 436/165; 422/82.01; 422/82.05; 422/82.11; 204/556; 204/400; 204/403; 356/317; 356/318; 356/445
[58] Field of Search ............................. 422/82.01, 82.02, 422/82.05, 82.09, 82.11; 436/73, 74, 149, 150, 151, 164, 165; 356/445, 447, 317, 318; 204/554, 556, 400, 403

[56] References Cited

U.S. PATENT DOCUMENTS

| | | | |
|---|---|---|---|
| 4,201,646 | 5/1980 | Matson | 204/406 |
| 4,804,443 | 2/1989 | Newman et al. | 205/789.5 |
| 4,844,613 | 7/1989 | Batchelder et al. | 356/318 |
| 4,889,427 | 12/1989 | Van Veen et al. | 356/445 |
| 4,931,384 | 6/1990 | Layton et al. | 435/7.31 |
| 4,997,278 | 3/1991 | Finlan et al. | 356/128 |
| 5,035,863 | 7/1991 | Finlan et al. | 422/82.05 |
| 5,047,213 | 9/1991 | Finlan et al. | 422/82.11 |
| 5,055,265 | 10/1991 | Finlan | 422/82.05 |

(List continued on next page.)

FOREIGN PATENT DOCUMENTS

| | | |
|---|---|---|
| 286195 A2 | 10/1988 | European Pat. Off. . |
| 395222 A2 | 10/1990 | European Pat. Off. . |

OTHER PUBLICATIONS

Jung et al. "Feasibility of an Integrated Optics Surface Plasmon Modulator." *Proc. SPIE–Int. Soc. Opt. Eng.*, vol. 2291, pp. 361–370, 1994.

Chadwick, B. and Gal, M. (1993), "An Optical Temperature Sensor Using Surface Plasmons," *Jpn. J. Appl. Phys.* 32:2716–2717.

(List continued on next page.)

*Primary Examiner*—Maureen M. Wallenhorst
*Attorney, Agent, or Firm*—Greenlee, Winner & Sullivan, P.C.

[57] ABSTRACT

This disclosure describes new methods and devices for sensing redox-active analytes in solution. The invention combines a surface plasmon resonance (SPR) sensor and a chemical electrode sensor. A conducting layer which supports SPR is attached to a voltage source. The voltage source is also connected to a reference electrode, which is in the aqueous solution with the SPR sensor. As the voltage is varied, the analytes undergo oxidation and reduction at the surface of the conducting film. The current is measured, just as it would be in a standard chemical electrode, with current peaks appearing at different potentials indicating different ions in the solution. Unlike a standard chemical electrode, the surface of the conducting film is also used to excite a surface plasmon wave (SPW). The SPW provides new information which is not available from any standard chemical electrode, such as the effective index of refraction at the surface of the conducting film as the analytes are being oxidized and/or reduced. This additional source of information can be used to minimize the effects of overlapping stripping peaks and interspecies compound formation as well as determine the thickness of surface layers during measurements. Additionally, the simultaneous determination of reaction properties and optical properties of reaction products can provide additional information about the aqueous support solution such as the quantity and types of natural oxidants in solution, such as oxygen or hydroxides. The formation of oxides and hydroxides will lead to measurably different optical properties.

6 Claims, 16 Drawing Sheets

U.S. PATENT DOCUMENTS

| | | | |
|---|---|---|---|
| 5,064,619 | 11/1991 | Finlan | 422/82.05 |
| 5,067,788 | 11/1991 | Jannson et al. | 385/2 |
| 5,313,264 | 5/1994 | Ivarsson et al. | 356/73 |
| 5,327,225 | 7/1994 | Bender et al. | 356/445 |
| 5,351,127 | 9/1994 | King et al. | 356/445 |
| 5,359,681 | 10/1994 | Jorgenson et al. | 385/12 |
| 5,374,563 | 12/1994 | Maule | 436/165 |
| 5,478,755 | 12/1995 | Attridge et al. | 436/518 |
| 5,485,277 | 1/1996 | Foster | 356/445 |
| 5,508,809 | 4/1996 | Peacock et al. | 356/445 |

OTHER PUBLICATIONS

Christian, G.D. (1986) in *Analytical Chemistry*, 4th ed., Chapter 12, "Electrolytic Methods," John Wiley & Sons, Inc., pp. 325–356.

Fontana, E. et al. (1988), "Characterization of dielectric–coated, metal mirrors using surface plasmon spectroscopy," *Appl. Opt.* 27(16):3334–3339.

Gordon, J.G., II and Ernst, S. (1980), "Surface plasmons as a probe of the electrochemical interface," *Surface Sci.* 101:499–506.

Jordan, C.E. et al. (1994), "Characterization of Poly–L–1–ysine Adsorption onto Alkanethiol–Modified Gold Surfaces with Polarization–Modulation Fourier Transform Infrared Spectroscopy and Surface Plasmon Resonance Measurements," *Langmuir* 10(10):3642–3648.

Jorgenson, R.C. and Yee, S.S. (1994), "Control of the dynamic range and sensitivity of a surface plasmon resonance based fiber optic sensor," *Sensors and Actuators A* 43:44–48.

Jorgenson, R.C. and Yee, S.S. (1993), "A fiber–optic chemical sensor based on surface plasmon resonance," *Sensors and Actuators* B 12:213–220.

Jorgenson, R.C. et al. (1993), "Multi–wavelength surface plasmon resonance as an optical sensor for characterizing the complex refractive indices of chemical samples," *Sensors and Actuators* B 13–14:721–722.

Jung, C.C. (1991), "Surface Plasmon Resonance," Master's thesis, University of Washington, 108pp.

Jung, C.C. (1994), "Surface Plasmon Resonance Light Modulators Using Electro–optic Polymers," Ph.D. dissertation, Chapter II, University of Washington.

Jung, C.C. et al. (1996), "Chemical electrode surface plasmon resonance sensor," *Sensors and Actuators* B 32:143–147.

Jung, C.C. et al. (1995), "Fiber–optic surface plasmon dispersive index sensor for highly opaque samples," *Process Control and Quality* 7:167–171.

Kretschmann, E. (1971), "Die Bestimmung optischer Konstanten von Metallen durch Anregung von Oberflächenplasmaschwingungen," *Z. Physik* 241:313–324.

Lambeck, P.V. (1992), "Integrated opto–chemical sensors," *Sensors and Actuators* B 8:103–116.

Lavers, C.R. et al., Galley Proof Version 20 Oct. 1994, "Electrochemically–controlled waveguide–coupled surface plasmon sensing,".

Lavers, C.R. et al. (1995), "Electrochemically–controlled waveguide–coupled surface plasmon sensing," *J. Electroanal. Chem.* 387:1–2,11–22.

Lavers, C.R. and Wilkinson, J.S. (1994), "A waveguide–coupled surface–plasmon sensor for an aqueous environment," *Sensors and Actuators* B 22:75–81.

Liedberg, B. et al. (1995), "Biosensing with surface plasmon resonance—how it all started," *Biosensors & Bioelectronics* 10:i–ix.

Mar, M. et al. (1993), "In–Situ Characterization of Multilayered Langmuir–Blodgett Films Using a Surface Plasmon Resonance Fiber Optic Sensor," *Proc. of the 15th Annual Conf. of the IEEE Engineering in Medicine and Biology Soc.*, San Diego, CA, pp. 1551–1552.

Marschall, N. and Fischer, B. (1972), "Dispersion of Surface Polaritons in GaP," *Phys. Rev. Lett.* 28:(13):811–813.

Moslehi, B. et al. (1991), "Optical Magnetic and Electric Field Sensors Based on Surface Plasmon Polariton Resonant Coupling," *Electron. Lett.* 27(11):951–953.

Matsubara, K. et al. (1988), "Optical chemical sensor based on surface plasmon measurement," *Appl. Opt.* 27(6):1160–1163.

Nelson, S.G. et al. (1996), "High Sensitivity Surface Plasmon Resonance Sensor Based on Phase Detection," *6th Int'l Conf. on Chemical Sensors*, Jul. 22, 1996, Washington D.C., 18pp.

Saban, S.B. et al. (1996), "Trace Ion Sensing in Aqueous Solutions Using a Novel Electrochemical–Surface Plasmon Resonance Sensor," Presented in 6th International meeting on chemical sensors, Jul. 22–25, 1996, *National Inst. of Standards and Technology*, Gaithersburg, MD, Abstract only.

Sambles, J.R. et al. (1991), "Optical excitation of surface plasmons: an introduction," *Contemp. Phys.* 32(3):173–183.

van Gent, J. et al. (1990), "Optimization of a chemooptical surface plasmon resonance based sensor," *Appl. Opt.* 29(19):2843–2849.

van Gent, J. et al. (1991), "Design and Realization of a Surface Plasmon Resonance–based Chemo–Optical Sensor," *Sensors and Actuators* A 25:449–452.

Wightman, R.M. and Wipf, D.O. (1989), "Voltammetry at Ultramicro–electrodes," *Electroanal. Chem.* 15:267–353.

Ishimaru, A. (1991), *Electromagnetic Wave Propagation, Radiation, and Scattering*, Prentice–Hall, New Jersey, pp. 43–45.

Lambeck, P.V. (1991), "Chemo–optical micro–sensing systems," SPIE vol. 1511, Fiber Optic Sensors: Engineering and Applications, pp. 100–113.

Kreuwel, H.J.M. (1988), "Planar waveguide sensors for the chemical domain," Ph.D., Thesis, Univerisyt of Twente, The Netherlands, 162pp.

Lange, P. et al. (1983), "Infrared attenuated total reflection spectroscopy at the metal–electrolyte interface," *Vacuum* 33:763–766.

Lavers, C. (1995) "A New Sensor for Medicine," *Electronics World + Wireless World* 101(1717):1021–1022.

SURFACE PLASMON RESONANCE CHEMICAL ELECTRODE

CROSS REFERENCE TO RELATED APPLICATIONS

This application claims the benefit of priority under 35 U.S.C. 119(e) of U.S. provisional application Ser. No. 60/007,029, which was filed under 35 U.S.C. 111(b) on Oct. 25, 1995.

BACKGROUND OF THE INVENTION

A surface plasmon wave (SPW) is a charge density (electromagnetic) wave, excited at the interface between a conductor or semiconductor, e.g. a metal surface, and a dielectric. (N. Marschall, B. Fischer, "Dispersion of surface polaritons in GaP," Physical Review Letters 28, pp. 811–813, March (1972). Surface plasmon waves (SPWs) can be optically excited by an evanescent field, created when light undergoes total internal reflection, for instance, off the base of a prism (Kretschmann, E. (1971), "Die bestimmung optischer konstanten von metallen durch anregung von oberflachenplasmaschwingugen," Z. Phys. 241:313), or as it propagates down a fiber optic. The evanescent field penetrates through the metal and excites an SPW on the outer surface of the metal where the metal meets the dielectric. In all SPR configurations, SPR can be excited only by transverse magnetic (TM) polarized light, that is, light which has its electric field polarized parallel to the incident plane. (If transverse electric (TE) light is present in the system, it does not carry any SPR signal. It could possibly be used as a reference signal.)

The SPW is a resonant phenomenon which depends on the indices of refraction and the thickness of the various layers, as well as the wavelength and the angle of incidence of the light. The dispersion equation for an SPW is given by Equation 1:

$$k_{sp} = k_o \sqrt{\frac{\epsilon_c \epsilon_d}{\epsilon_c + \epsilon_d}}$$

where $k_o$ is the free space wavevector ($k_o = \omega/c$); $\epsilon_c$ and $\epsilon_d$ are the complex permittivities of the conducting and the dielectric layers, respectively; and $\omega$ is the angular frequency. In order to excite the SPW, the parallel component of the incident wavevector $k_\parallel$, must equal the surface plasmon wavevector $k_{sp}$. The parallel component of the incident wavevector can be expressed as Equation 2:

$$k_\parallel = \frac{2\pi n \sin(\theta)}{\lambda}$$

where n is the index of refraction of the medium in which the light is incident, $\theta$ and $\lambda$ are the angle of incidence and wavelength of the light, respectively.

It can be seen from Eq. (2) that the resonance condition can be met by either varying the angle or the wavelength of the incident light, until $k_{sp} = k_\parallel$. These techniques are referred to as angle modulation and wavelength modulation, respectively.

The SPW is highly localized at the surface of the conducting layer, e.g. a metal film. The intensity of the electric field of the SPW decays exponentially into the solution surrounding the dielectric. The characteristic decay length is given by (Raether, H. (1977), *Physics of Thin Films*, Academic Press, New York, p. 164) Equation 3:

$$L = \frac{1}{2Re\left(\sqrt{k_{sp}^2 - k_s^2}\right)}$$

where L represents the distance at which the intensity of the SPW has decayed to $e^{-1}$ times its value at the conductor/dielectric interface. The wavevector $k_s = k_o n_s$ is the wavevector in the solution surrounding the sensor. Re refers to the real part of the quantity in paratheses. For example, if the surrounding medium is water and the conductor is gold, L=831 Å at a wavelength of 6328 Å. This makes it possible to determine very small changes in the effective index of refraction within approximately 2000 Å of the gold surface. For example, surface plasmon resonance (SPR) sensors have been used to detect monolayer growth of Langmuir-Blodgett films (Mar, M. et al. (1993), "In-situ characterization of multilayered Langmuir-Blodgett films using a surface plasmon resonance fiber optic sensor," Proc. of the 15th Annual Conf. of the IEEE Engineering in Medicine and Biology Soc., San Diego, Calif, pp. 1551–1552).

Sensors based on the surface plasmon resonance (SPR) effect sense the refractive index (RI) of a thin region adjacent to the sensing surface (Sambles, J. R. et al. (1991), "Optical excitation of surface plasmons: an introduction," Contemporary Physics 32:173–183). SPR can be applied indirectly to other sensing applications by treating or manipulating the sensing surface such that the refractive index at the surface varies with the presence of the substance to be sensed. For instance, the surface can be made sensitive to a particular antibody by coating the surface with an antigen for that antibody. When the antigen binds to the antibody, the refractive index at the surface changes slightly. A commercial application of SPR to biological sensing has been developed using this principle (Liedberg, B. et al. (1995), "Biosensing with surface plasmon resonance—how it all started," Biosensors and Bioelectronics 10:i–ix). Other applications as diverse as sensing of ammonia (Van Gent, J. et al. (1991), "Realization of a Surface Plasmon Resonance-based Chemo-Optical Sensor," Sensors and Actuators A 25–27:449–452), magnetic and electric fields (Moslehi, B. et al. (1991), "Optical magnetic and electric field sensors based on surface plasmon polariton resonant coupling," Electronics Letters 27:951–953), and temperature (Chadwick, B. and Gal, M. (1993), "An optical temperature sensor using surface plasmons," Jpn. J. Appl. Phys. 32:2716–2717) similarly rely on sensitive overlayers.

The practical effect of a change in the RI of the dielectric adjacent to the SPR sensing surface is a shift in the SPR resonance curve. If the wavelength modulation technique is being used, the resonance curve of interest is the reflected intensity of light versus the incident wavelength. The minimum of this curve is defined as $\lambda_{sp}$, which is the SPR resonance minimum in wavelength space. If the angle modulation technique is being used, the resonance curve of interest is the reflected intensity of light versus the incident angle. The minimum of this curve is defined as $\theta_{sp}$, which is the SPR resonance minimum in angle space. It is also possible to determine the resonance from looking at the transmitted light intensity using either of these techniques. The techniques can also be combined, in which case the three dimensional intensity-angle-wavelength space must be considered. The absorption of the dielectric layers, which is directly related to the imaginary part of the refractive index of the dielectric layers, can also be determined from the SPR resonance. More absorbing dielectric layers, such as dye indicators (for instance, methylene blue), cause broader, less deep resonances. Parameters such as the resonance depth $\delta_{sp}$, or the resonance width $W_{sp}$, are not used as much as the resonance minimum location given by $\lambda_{sp}$ or the resonance angle given by $\theta_{sp}$, because SPR is much more sensitive to changes in the real part of the index of refraction than it is to changes in absorption (see C. C. Jung, "Surface plasmon resonance," Masters Thesis, University of Washington (1991), C. Jung, R. Jorgenson, C. Morgan, and S. Yee, "Fiber optic surface plasmon dispersive index sensor for highly opaque samples," Process Control and Quality, 7, pp. 167–171 (1995).

In general, SPR sensors have been commonly used in two main applications: 1) measuring the refractive index of chemical samples and 2) monitoring the growth of thin biochemical or inorganic films on the surface of the sensor.

In general, an SPR configuration includes a source of electromagnetic radiation (light), an optically transmissive (transparent) component (the SPR sensor) which has a conducting film (e.g. a metal layer) on it, and a detector. The conducting film is in contact with a dielectric. Light is transmitted into the transparent component, undergoes total internal reflection, and if the conditions outlined in the equations above are met, then a surface plasmon wave will occur at the surface of the conducting film, that is at the interface of the metal layer and the dielectric. The detector measures the resonant phenomenon.

Surface plasmon resonance (SPR) can be performed in many different configurations. U.S. Pat. No. 4,844,613 discloses an SPR sensor configuration wherein the sensor includes a prism, one surface of which is coated with index matching fluid which is then covered with a glass microscope slide or cover slip. The exposed surface of the slide is then coated with a conductive layer (metal) on which SPR occurs. The metal layer can be coated with a sensitive layer, e.g. an antibody. The sensor is exposed to a test solution. If the antibody binds an antigen in the test solution, the thickness of the sensitive layer is changed, causing a change in the refractive index and a corresponding change in the SPR resonance angle.

U.S. Pat. No. 5,035,863 discloses an SPR sensor configuration adapted for biochemical testing on large samples, such as electrophoresis gels, allowing for sequencing of the gel based on changes in refractive index. The sensor includes several layers: a transparent plate, a metal layer of a mosaic of silver dots, and sandwiched in between is the gel. Light is directed and undergoes total internal reflection at the interface of the transparent plate and the metal layer and SPR occurs at the metal layer.

U.S. Pat. No. 4,997,278 discloses an SPR sensor configuration to detect the progression of a reaction between a sample and a sensitive layer, e.g. an antibody layer. An optically transmissive component comprises a hemicylindrical lens and slide. The slide is coated with a reflective layer (metallic film). A sensitive layer, the refractive index of which changes as the reaction, e.g. antigen binding to antibody, is applied to the surface of the reflective layer. The sensitive layer is smaller than the reflective layer. Collimated light is introduced via a lens which focuses the incident light to a point to form a fan-shaped area of light incident at the point. The light undergoes total internal reflection at the point and exits from the component. A detector array monitors the angle of incidence of the light at the point of SPR, together with a range of angles about it, to detect the progression of the resonant phenomenon, an indicator for the reaction between the sensitive layer (e.g. antibodies) and the sample (e.g. antigen).

U.S. Pat. No. 5,064,619 discloses another SPR sensor configuration which can be used to monitor the progress of a reaction, e.g. the binding of a sample to a sensitive layer (for instance, the binding of an antigen to an antibody). A laser is used to generate light which is reflected off a concave reflector to a point or line on the interface between a metal layer and a glass slide. A single beam of laser light is scanned by a movable mirror across an arc to cover the angles of incidence within which SPR occurs. The sensitive layer is coated on top of the metal layer, and a sample is passed across the sensitive layer. Any reaction (binding of antigen to antibody, for instance) causes a change in the refractive index of the layer. This change is detected by measuring the strength of the beam reflected from the point or line of incidence.

U.S. Pat. No. 5,055,265 discloses an SPR sensor configuration utilizing long-range SPR to follow the progress of a reaction, again between a sensitive layer and a test sample. This configuration includes a source of light, and a sensor which includes a block of transparent material, a dielectric membrane layered on the block, which membrane is coated with a layer of metal (only about 17 nm thick, versus about 56 nm for short range SPR). On top of the metal layer is a sensitive layer, e.g. antibody layer. Again, a sample to be tested is contacted with the combined layers (metal and sensitive) to test for the presence of a specific material. A radiation source and detector complete the configuration, allowing for measurement of the angle of incidence. Long-range SPR provides increased sensitivity.

U.S. Pat. No. 5,478,755 provides another SPR sensor configuration utilizing long-range SPR to monitor the progress of a reaction between a sensitive layer and a test sample (an immunoassay).

U.S. Pat. No. 5,047,213 discloses an SPR sensor configuration for biological sensing. This sensor uses an optical waveguide, e.g. a fiber optic. Electromagnetic radiation is introduced into the input end of the waveguide. The output end of the waveguide is cut off at an angle at its axis so that it has a sloping face, which is coated with a layer of metal, which itself is coated with a sensitive layer. The light undergoes total internal reflection at this face. A sample to be tested is contacted with the multi-layer. The light incident on the face leads to SPR, and the reaction of the sample with the sensitive layer can be monitored thereby.

U.S. Pat. No. 5,313,264 discloses another SPR sensor configuration for biological sensing. The configuration includes a sensor unit with at least two sensing surfaces, a source of light, and a lens for focusing the light into a wedge-shaped streak of light which extends transversely over all the sensing surfaces. A two-dimensional matrix of individual photodetectors provides the detecting device. An anamorphic lens system images rays of reflected light from the sensing surfaces onto each of its columns of photodetectors, thus each sensing surface has a corresponding set of columns of photodetectors. An evaluation unit determines the minimum reflectance or angle of resonance at each sensing surface.

U.S. Pat. No. 5,327,225 discloses an SPR sensor configuration in which a fiber optic is connected at one end to a laser, and at the other end to a detector. The fiber optic is coated with a metal layer and with an overlay or underlay material. The sensor can be used in biochemical and chemical applications when a test sample contacts the sensor. The overlay or underlay material can be like the sensitive layers of the above-mentioned disclosures, e.g. antibody or antigen layer. As in the above-mentioned disclosures, binding of antigen to antibody, for instance, changes the refractive index of the sample and thus the SPR signal.

U.S. Pat. No. 5,485,277 discloses an SPR sensor configuration which also can be used as a biosensor. It includes a metal film coated waveguide cartridge. The waveguide cartridge includes a planar waveguide coated with a metal film. The waveguide has a plurality of reflector surfaces within it. A sample flow cell is adjacent to the waveguide cartridge. A source of TM-polarized light is optically connected to the waveguide. A cylindrical diverging lens is optically connected to the waveguide. A plurality of photodetectors is optically connected to the cylindrical diverging lens. This configuration provides reflector surfaces within the waveguide and the SPR interface directly on the waveguide.

The SPR sensor of this invention can be, among others, a prism, waveguide, or light pipe. It can be single mode or multi-mode. It can be zero-order or first-order. U.S. provisional application Nos. 60/005,878, 60/007,027, 60/009,169 and corresponding U.S. applications (attorney docket nos. 89-95, 89A-95, and 101-95, respectively) filed Oct. 25, 1996, and incorporated in their entirety by reference herein disclose zero-order and first-order planar lightpipe sensors. These sensors can utilize various optical input and detection schemes.

If there are several different species present in solution at the surface of the sensor, the sensor will measure an effective index of refraction which is a function of all the species. In order to get around this lack of selectivity, many researchers have functionalized the surfaces of the SPR sensors, so that they selectively bind specific molecules (Jordan, C. E. et al. (1994), "Characterization of Poly-L-lysine adsorption onto alkanethiol-modified gold surfaces with polarization-modulation fourier transform infrared spectroscopy and surface plasmon resonance," Langmuir 10:3642–3648). This typically involves complicated and time-consuming chemistry, and can result in sensors that are stable over only a short period of time.

As an alternative to this approach, the present invention combines electrochemical methods and SPR to detect unknown species.

BRIEF SUMMARY OF THE INVENTION

The present invention provides a sensor device which detects both SPR and electrochemical phenomena. The device and methods of the present invention can be used to detect unknown species (uncharged and redox-inactive) by known SPR techniques. Additionally, the device and methods of the present invention can be used to detect and identify unknown species in solution which are capable of undergoing oxidation and/or reduction. The SPR and electrochemical measurements can be performed simultaneously or serially. This invention provides for measurement of electrochemical properties of unknown species giving rise to SPR effects and for measurement of SPR as a function of electrochemical behavior. The device of this invention allows for applying a voltage to the SPR sensor (thereby attracting polarizable and/or ionic species) and monitoring the SPR signal either during the application of the voltage, as a function of time or as a function of voltage, or monitoring the SPR signal at any point before or after application of voltage to the sensor. The device of the present invention allows for using an electrochemical electrode actively, to create a product (by plating a product onto the sensing area) whose optical properties can be measured. That is, the device of the present invention allows for measurement of the RI of whatever material is in the range of the SPW which can be calculated by Equation 3. If there is an analyte reduced on the conducting layer which is not as thick as the penetration depth of the SPW as given by Equation 3, then the SPW will measure an effective index of refraction which is a function of both the RI of the reduced layer and the RI of the solution. Any art-known SPR configuration can be adapted for use in the sensor device and methods of the present invention. Many electrochemical techniques and devices can be combined with any SPR configuration to provide the SPR sensing devices and methods of the present invention.

The present device includes a surface plasmon resonance sensor comprising a sensing area, e.g., any conducting or semi-conducting material that supports SPR; a source of electromagnetic radiation fixed in a position relative to the surface plasmon resonance sensor and arranged in such a way as to direct the electromagnetic radiation through the surface plasmon resonance sensor to achieve total internal reflection and excite surface plasmon resonance at the sensing area; a means for applying a constant or variable voltage to the sensing area and to a reference electrode and optionally an auxiliary electrode; a means for monitoring a surface plasmon resonance signal exiting the surface plasmon resonance sensor; optionally, a means for monitoring an electric current resulting from the application of the voltage to the sensing area; wherein the surface plasmon resonance sensor and the reference and auxiliary electrodes are in contact with a solution containing polarizable, ionic or redox-active analytes.

The means for applying a voltage can be chosen from among many techniques by one of ordinary skill in the art. One means for applying voltage is the technique known as anodic stripping voltammetry. Anodic stripping voltammetry is a standard method used in electrochemistry to measure the presence of unknown ions in solution. In this technique a negative voltage is applied to a (working) electrode, relative to a reference electrode in solution. (In the case of the present invention, the working electrode is the SPR sensor sensing area.) The potential of the working electrode (SPR sensing area) can be controlled relative to the reference electrode by adjusting the applied voltage between the working electrode and an auxiliary electrode. A potentiostat allows for the measurement of the potential difference between the working and reference electrodes with minimum loss due to solution resistance.

In anodic stripping voltammetry, redox-active analytes, such as metal cations, are electroplated onto the surface of an electrode and then electrically stripped off. The current which flows during the stripping process is proportional to the analyte concentration, and the voltage at which the stripping occurs corresponds to the redox potential unique to the analyte. A negative voltage is applied long enough so that positive ions in solution are reduced and concentrated at the surface of the electrode. Following the reduction step, the voltage is scanned/incremented in positive steps at specified time intervals, while simultaneously measuring the current flow in the electrode. A current peak occurs at the Nernst potential, which corresponds to the oxidation of ions back into solution. Based on the potentials at which the current peaks occur, it is possible to identify the different ions in solution. The height of the current peak is linearly proportional to the concentration of the ions. In order to use this technique with an SPR sensor, the conducting or semi-conducting surface of the SPR sensor is contacted electrically, so that it acts both as a chemical electrode, and as a conducting surface which supports SPR.

The sensor device of the present invention may use monochromatic or non-monochromatic, e.g., multiwavelength light. A multiwavelength source of light includes broad band light, white light, and a combination of discrete monochromatic sources. If monochromatic light is used, then the angle of incidence is monitored to detect the SPR signal. If multiwavelength light (wavelength modulation) is used, the angle of incidence is held constant and the wavelength which shows minimum reflective intensity is a measurement of the SPR signal.

The SPR sensor itself can be chosen from among any materials which allow for total internal reflection of the light introduced into it. Suitable SPR sensors include, but are not limited to, prisms, waveguides, light pipes and fiber optics. Both single mode and multi-mode sensors can be used; multi-mode sensors are preferred. Any SPR configuration, including angle modulation, wavelength modulation, phase modulation configurations, zero and first order sensors can be used in the present invention.

In the sensor device of the present invention, electrical contact must be made between the SPR sensing area (the metal/conducting film) and a source of voltage. When the wavelength modulation technique is being used, light is ideally incident at a single fixed angle. This is not possible with a multi-mode fiber optic. The range of angles which are present at the fiber optic core/conducting interface cause a broadening of the SPR resonance signal. This is a source of noise in this system.

Surface plasmon waves can be excited by several different configurations of the elements/equipment required to induce and detect SPR. Any configuration which will support SPR can be used to create the SPR sensor of the present invention. In all cases the basic principle of operation is the same. A thin layer of a conducting or semi-conducting material which supports SPR is coated onto an SPR sensor to make a sensing area which supports the SPR. A conducting material is preferred. For example a thin layer of metal may be evaporated onto the base of a prism, or the core of a waveguide or light pipe. Gold is a preferred material for this film due to its high conductivity and stability. Although silver is a suitable material for supporting SPR, silver oxidizes quickly in air and in solution, thereby making it less preferred for the electrochemical SPR sensor device of this invention. A thin adherence layer (20 to 30 Å) of chrome or titanium may be put down first for the purpose of adherence. The SPW is excited on the surface of the conductor by light incident in the waveguide, or on the base of the prism. The optical signal from the SPR is used to determine the effective index of refraction at the surface of the conducting film. The change in the effective index of refraction is a function of the index of refraction of all materials within the range of the SPW. This includes the reduced, oxidized or adsorbed material at the surface of the conductor as well as the dielectric surrounding it.

The sensing area that supports the SPR is contacted electrically, e.g., by a metal wire or strip line connected at one end to the sensing area and at the other end to the voltage source, so that a voltage may be applied to the film relative to a reference electrode. By measuring the current as a function of the applied voltage, different chemical ions can be identified in solution as they are reduced and oxidized at the surface of the conducting film. This is a standard technique known as anodic stripping voltammetry. This process is greatly enhanced by performing the measurement on the SPR surface.

The advantages of the sensor device of the present invention are many. When used to perform anodic stripping voltammetry, for instance, the present sensor device allows for the monitoring of a redox reaction (electrochemically, by measuring the current across the electrochemical sensor which is the sensing area of the SPR sensor), and it also allows for monitoring the product of the redox reaction (optically, by measuring a physical property, i.e. the refractive index, of the product of the redox reaction). Monitoring both the reaction and the product of the reaction, electrochemically and optically, respectively, is accomplished by a single sensor device. The combination of these two types of measurements by a single sensor device is useful in a variety of applications.

For example, if a solution is being tested for the presence of metals and two of the metals form intermetallic compounds, the present sensor device will detect the plating of the two metals on the sensor's sensing surface. If the intermetallic compound is stable and does not oxidize off the sensing surface, this is detected optically because the SPR signal does not return to its baseline value.

Interspecies compound formation can be characterized by a comparison to the baseline response of the sensor of this invention. Since an interspecies compound is neutralized at the electrode surface, oxidation or reduction of the compound does not occur. An example is the CuZn intermetallic compound. When Cu and Zn are in solution together, the simultaneous determination of the two metals results in depression of the stripping peaks as the intermetallic compound is formed at the electrode surface. This effect makes concentration determinaton difficult when the intermetallic compounds have different stoichiometries. When the compounds remain at the surface of the electrode after stripping, a comparison of the SPR wavelengths just prior to and after stripping reveals a difference between baseline and final signals. This information can yield the index of refraction and the thickness of the remaining compound and thus aid in quantifying the concentrations of the analytes in solution. Therefore, the ability to measure simultaneously both reactions and products of reactions with the same sensor is a major advantage of the present sensor over other art-known sensors.

Another example of the usefulness of the present sensor device is that if two redox-active analytes have very similar oxidation potentials, and therefore are difficult to identify using electrochemical data alone, the optical data from the SPR can be used to identify them, when the SPR is monitored in conjunction with performing anodic stripping voltammetry. For instance, arsenic and mercury have similar oxidation potentials, but as the voltage is ramped and the oxidation potential of these two metals is approached, a bipolar shift in the SPR signal is seen.

Because the SPR signal measured during anodic stripping voltammetry (ASV) measures the optical properties of the product of a redox reaction, the combined electrochemical-SPR measurement provides additional information that neither the electrochemical nor SPR measurement can provide alone. This information can be used to resolve several difficulties that have plagued stripping voltammetry techniques including overlapping stripping peaks and the formation of interspecies compounds at the surface of the electrodes. Overlapping stripping peaks occur when the redox potentials of two or more analytes are sufficiently close such that the corresponding current peaks overlap. In unknown solutions, overlapping peaks may be misinterpreted as a single peak and therefore provide incorrect information about the analytes. The electrochemical-SPR sensor device of the present invention can minimize this effect by using the additional information on the optical properties of analytes in question. As mentioned above, an example of this effect is the simultaneous determination of As and Hg in an HCl electrolyte. During an experiment using the sensor device of this invention, the analysis of Hg shows a decrease in SPR wavelength with respect to the electrolyte baseline as Hg is plated on, while analysis of As in the same solution shows an increase in SPR wavelength with respect to the baseline. If the baseline SPR wavelength is subtracted out, the values of the SPR wavelength can take on positive and negative values. Utilization of this information can be extremely effective in identifying and characterizing overlapping peaks.

Another example of the usefulness of the present sensor device is in a situation in which a redox-active analyte, for instance, a metal is plated onto the sensing surface. Then, instead of ramping the voltage to oxidize the metal off the surface, oxidants in the sample solution are allowed to oxidize the metal. The products of these oxidation reactions can be monitored optically, by measuring the refractive index of the solution near the sensor.

The SPR signal provides current independent measurements of the concentration of redox-active and adsorbed analytes, as well as the thickness of the reduced film. SPR has a high sensitivity which can be used to detect monolayer thicknesses of the reduced material on the conducting surface, making it possible to sense analyte concentrations as low as one part per billion. SPR also has the advantage of being able to detect neutral (and redox-inactive) molecules at the surface which standard chemical electrodes cannot detect.

BRIEF DESCRIPTION OF THE SEVERAL VIEWS OF THE DRAWINGS

FIG. 2B is that the remaining leg from the reflected light exiting the splitter is used as a reference signal by transmitting it to the spectrograph (detector) as opposed to dumping it. The voltage source, current meter and reference electrode are not shown.

DETAILED DESCRIPTION OF THE INVENTION

Figure 1:
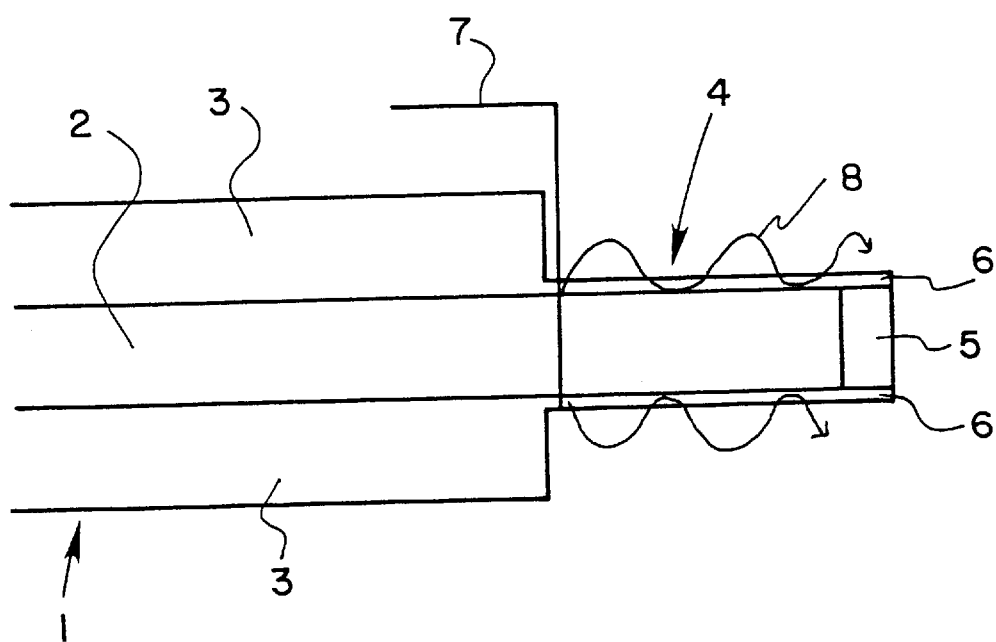
FIG. 1 is a cross-sectional view of an SPR fiber optic sensor showing the SPW (wavy arrow) excited on the surface of a thin conducting or semi-conducting film which has been evaporated onto the core of the fiber optic.

This invention is directed to sensor devices and methods useful for the measurement of SPR and electrochemical phenomena to detect and identify unknown polarizable, ionic or redox-active analytes in a sample. The sample can be solid, liquid or gas; gas, specifically includes plasma; and any solid would have to allow for diffusion of analytes through it, for instance doped polymer. "Redox-active analytes" are chemical species capable of being reduced and/or oxidized. Redox-active analytes include, but are not limited to, metals and metals ions, organic compounds capable of being reduced and/or oxidized, and inorganic compounds capable of being reduced and/or oxidized. Examples of redox-active analytes include, but are not limited to, titanium, chromium, manganese, iron, cobalt, nickel, copper, zinc, rubidium, lead, iridium, quinones such as benzoquinone, phenylene diamines, myoglobin, hemoglobin, dithiothreitol, metal complexes with organic ligands such as iron-phenanthroline (ferriin-ferroin) and ferricyanide-ferrocyanide. Polarizable analytes are chemical species capable of assuming/acquiring a partial positive or partial negative charge, with the result that a dipole is induced in the molecule. Polarizable analytes include, but are not limited to, halogenated organic compounds. Ionic species are chemical species which are charged, i.e. have either a positive or negative charge. Ionic species include, but are not limited to, positively charged amines or quaternary ammonium compounds, or negatively charged alkoxides.

In the devices of the present invention, the conducting or semi-conducting film which supports the SPR is contacted electrically with a metal wire (illustrated in FIG. 1) or strip line, so that a voltage may be applied to the film relative to a reference electrode. By measuring the SPR resonance when a voltage is applied to the SPR generating surface, different polarizable, ionic or redox-active species can be detected in solution. This may be, but does not necessarily have to be, done in parallel with any of the existing electrolysis techniques.

The sensing area of the SPR sensor comprises a layer of conducting or semi-conducting material. (The sensing area may also include a sensitive layer, e.g. having antibodies or other ligand-binding molecules, as is known to those skilled in the art.) For simplicity, unless otherwise explicitly stated, all references to "conducting" film or material are herein defined to include also semi-conducting materials. It is preferable to use a conducting, rather than a semi-conducting material, for the sensing area. The sensing area of the SPR sensor is the part of the SPR sensor which supports SPR and also is the site of oxidation and reduction of redox-active analytes. A thin layer of the conducting film which supports SPR is coated onto the SPR sensor, e.g. the base of a prism, or the core of a waveguide. Gold is a preferred metal for the conducting film, due to its high conductivity and stability. Silver is also a preferred metal for SPR, but has limited use in electrochemical measurements. A thin layer (20 to 30 Å) of chrome or titanium may be put down first, for the purpose of adherence. Then a layer of conducting metal, e.g. gold, approximately 55 nm thick is evaporated onto the surface of the SPR sensor. The SPW is excited on the surface of the conductor by light incident in the waveguide, or on the base of the prism. The optical signal from the SPR is used to determine the effective index of refraction at the surface of the conducting film. The effective index of refraction is a function of the optical properties of the reduced analyte, the optical properties of the supporting electrolyte, and the thickness of the reduced material at the surface of the conductor.

The SPR sensor itself can be chosen from among any sensor material which allows for total internal reflection of light. Sensors of this invention include, but are not limited to, prisms, waveguides, and light pipes. Waveguides include, but are not limited to, slab, planar, cylindrical, ion-diffused, rectangular, or elliptical. They may be fabricated out of any material which is transparent or semitransparent to the wavelength of light being used. These materials include, but are not limited to, glasses, crystals, semiconductors, plastics, or liquids confined by a rigid structure which has a lower index of refraction than the liquid. Lightpipes may be of any shape and can be made of any of the transparent or semi-transparent materials described above. They are not single-mode, but rather support a continuous range of angles, as discussed in more detail below.

The term "waveguide" refers to a three dimensional structure which is constructed in such a manner that it confines optical energy, allowing it to be transported from one point to another with minimal loss. Waveguides can be fabricated in many different shapes. These include, but are not limited to, structures with planar, rectangular, cylindrical, or elliptical cross sections. A waveguide may support several modes or a single mode. These are known as "multi-mode" and "single-mode" waveguides, respectively.

The term "mode" can be defined by the following explanation: A waveguide will allow light to propagate in only certain directions inside the waveguide, for a given wavelength of light. These directions are typically specified by the propagation vector, K. The allowed K-values for a given waveguide are discretized, just as the allowed energy levels of an electron in an atom are discretized. The K-values for a given waveguide can be determined by someone skilled in the art, by solving Maxwell's equations subject to the appropriate boundary conditions for the waveguide. If the solution allows for only one K-value, the waveguide is said to be "single-mode" at that wavelength of light. If more than one K-value is allowed, the waveguide is said to be "multi-mode." Typically, waveguides whose dimensions are on the order of the wavelength of light support only one or two modes. If the dimensions of the waveguide become too big, the modes will become so numerous and closely spaced that they are essentially continuous (just like the allowed energy levels of a free electron). In this case, the structure may be referred to as a "light pipe," rather than a waveguide. Unlike a waveguide, a "light pipe" will allow a continuous range of directions of light propagation within its boundaries, due to its dimensions being large in comparison to the wavelength of the light.

Surface plasmon resonance has been extensively used to determine the refractive index of unknown chemical samples. This technique has recently been implemented with a multimode fiber optic (Jorgenson, R. C. and Yee, S. S. (1993), "A fiber optic chemical sensor based on surface plasmon resonance," Sensors and Actuators B 12:213–220; Jorgenson, R. C. and Yee, S. S. (1994), "Control of the dynamic range and sensitivity of a surface plasmon resonance based fiber optic sensor," Sensors and Actuators A 43:44–48; Jorgenson, R. C. et al., U.S. Pat. No. 5,359,681, which are specifically incorporated in their entirety herein by reference ) using a white light source and a grating. The wavelength at which the surface plasmon is excited is a function of the index of refraction of the chemical sample surrounding the SPR fiber optic sensor. By comparing the spectrum of light entering and exiting the SPR sensor, the effective index of refraction surrounding the fiber optic sensor can be determined, at a single wavelength.

Any SPR configuration known in the art can be used in the present invention. Various angle modulation and various wavelength modulation configurations are well-known in the art (U.S. Pat. No. 4,844,613; U.S. Pat. No. 5,359,681). Another SPR configuration utilizes phase modulation to excite and monitor SPR (U.S. Pat. No. 5,374,563).

Another SPR configuration, known as the Kretschmann configuration, utilizes monochromatic light and hence angle modulation or multiwavelength light and hence wavelength modulation. It involves the use of a prism, upon the base of which has been deposited a thin layer of highly reflective metal, e.g. gold or silver. The metal surface is then contacted with a dielectric. The SPR signal can be monitored by directing TM polarized, monochromatic light into the prism and then measuring the intensity of the reflected light as a function of the angle of incidence. The resonance angle, e.g. the angle at which maximum coupling between the incident light and the surface plasmon waves occurs, is the angle of minimum reflective intensity. The SPR signal, in general, refers to the resonance which occurs in the reflected intensity as a function of incidence angle, incident wavelength, or phase of incident light. The signal is carried in both the transmitted light and in the reflected light.

The electrochemical technique which can be combined with the SPR measurement can be chosen from among many known to those skilled in the art. Those skilled in the art can adapt the device of the present invention to accommodate the particular electrochemical technique. The type of analyte to be detected and/or identified will affect the choice of electrochemical technique to be employed. For instance, anodic stripping voltammetry is employed when the redox-active analyte is a metal, while cathodic stripping voltammetry is used for detection of anions, such as chloride and bromide. These techniques include, but are not limited to, electrogravimetry; controlled-potential coulometry; controlled-current coulometry; voltammetry; anodic- and cathodic-stripping voltammetry; cyclic voltammetry; square wave voltammetry; differential pulse voltammetry; adsorptive stripping voltammetry; potentiometric stripping analysis and amperometry. Brief descriptions of these electrochemical techniques are given below, but the reader is directed to (Gary D. Christian, *Analytical Chemistry*, 4th ed., John Wiley and Sons, Inc. (1986)), which is incorporated in its entirety by reference herein, for more detailed discussions of these techniques.

In electrogravimetry, a metal is quantitatively plated onto a cathode; the amount of metal in a sample solution is determined by the gain in weight of the cathode (which in the present invention is the SPR sensor).

Controlled-potential coulometry is similar to electrogravimetry, but electrodeposition is not required. The potential of the working electrode (SPR sensor) is adjusted to the potential at which the analyte is either oxidized or reduced, and the electrolysis is allowed to go to completion. As in the other electrochemical techniques, it is preferred to avoid saturation of the sensing area with analyte. Instead of weighing the electrode (SPR sensor) to determine the amount of metal plated onto it, a coulometer is placed in series with the electrolysis circuit. A coulometer measures the quantity of charge flowing through the electrode. This measurement provides the total charge which has flowed during the reduction or oxidation process which is an indication of the total amount of redox-active analyte present.

Controlled-current coulometry, also known as coulometric titration, is a titration wherein the buret and the titrant solution are substituted with a constant-current source and a timer, and a pair of electrodes and electrolyte. The titrant is then generated electrochemicalally.

Voltammetry refers to a class of electroanalytical techniques in which the current at a working electrode in solution is measured as a function of a potential waveform applied to the electrode. The resulting current-potential curve is called a voltammogram and correct interpretation provides information about the reaction occurring at the surface of the electrode. In a typical voltammetric experiment, oxidation or reduction of analytes occurs at the surface of a working electrode when the electrode is biased near the redox (Nernst potential) of a given analyte. At this potential, electron transfer takes place and a measurable change in current occurs whose magnitude is linearly proportional to the concentration of the given analyte in solution. Therefore, the magnitude of the current peak provides concentration information while the potential at which the current peak occurs identifies the analyte. Additional information such as the reaction type (reversible, quasi-reversible, and irreversible) and analyte mass-transport rates (diffusion coefficients) can also be obtained depending on the type of voltammetric experiment performed. Since most analytes have different redox potentials, voltammetry allows the measurement of multiple analytes in solution. Limitations on the number of analytes determinable in a given solution are due to the electrochemical properties of the electrode material. At negative potentials, in protic solutions, the limitation is hydrogen evolution current, while at positive potentials, the limit is due to electrode oxidation or dissolution. While these limits are a strong function of electrode material and solution pH, the absolute potential limits based on electrode materials with the best negative and positive potentials are from −1.8 to +1 V. For electrodes based on gold, the potential limit is typically from −0.5 to 0.8 V though these limits may be expanded with a suitable choice of supporting electrolyte. For silver the limits are −0.2 to 0.5 V. Silver is usually a poor choice for electrochemical experiments since silver is relatively easily oxidized.

There are several variations of voltammetric measurements, and most of these are due to changes in the type of potential waveform used (cyclic, staircase, AC, squarewave, pulse, and differential pulse voltammetry) and/ or the addition of a preconcentration step (stripping voltammetry). Consequently, the choice of technique determines how many characteristics of the redox reaction can be measured and how well a given characteristic can be measured. The most versatile of the voltammetric measurements, in terms of the number of measurable characteristics, is cyclic voltammetry.

Cyclic voltammetry consists of scanning linearly the potential of a stationary working electrode using a triangular potential waveform. The resulting voltammogram provides information about both the oxidation and reduction reaction which includes the thermodynamics of the redox processes, the kinetics of heterogeneous electron transfer reactions, analyte identification and quantitation, and analyte diffusion coefficients. Variations on cyclic voltammetry involve a change in the waveform used to minimize the effects of non-faradaic currents in the measurement. The primary cause of these non-faradaic currents is a capacitance that is inherent in any electrochemical measurement system and is caused by the formation of a layer near the surface of the electrode that is devoid of analyte. This capacitance is in parallel with the solution resistance and causes a charging or discharging current anytime the potential is changed. The time constant of the charging current is a product of the solution resistance (R) and the diffusion layer capacitance (C), and therefore any sampling of the current should occur at a time after a change in potential that is greater than the RC time-constant.

Pulse voltammetric techniques substantially increase the ratio between faradaic and non-faradaic currents by taking advantage of the fact that the faradaic current decays more slowly than the non-faradaic current. The various pulse techniques are all based on a sampled current potential-step experiment. A sequence of such potential steps is applied to the working electrode. After the potential is stepped, the charging current decays rapidly to a negligible value while the faradaic current decays more slowly. Thus by sampling the current late in the pulse life, an effective discrimination against charging current is achieved. Variations of the pulse techniques include differential pulse, staircase, and square-wave voltammetry. Each variation seeks to discriminate against charging current while increasing the detection limits possible in the measurement.

In differential pulse voltammetry, fixed magnitude pulses are superimposed on a linear potential ramp. The current is sampled twice, just before the pulse application and again late in the pulse life. The first current is then subtracted from the second and the resultant current is plotted vs. applied potential. The technique has the advantage of discriminating against the charging current and subtracting out additional background noise due to trace impurities in the solution. Therefore overall sensitivity is improved. Drawbacks in the method include a significantly reduced scan rate which can cause longer measurement times.

Staircase voltammetry involves the use of successive potential steps about 10 mV in height with durations from 1 microsecond to 50 ms. The current is sampled at the end of each potential step where the charging current has decayed to a negligible value. The advantage of this method is much higher scan rates, but this comes at the expense of sensitivity because the background current is not subtracted out.

Squarewave voltammetry is a method which combines the speed of staircase voltammetry with the increased sensitivity of differential pulse voltammetry. In this technique, a symmetrical squarewave is superimposed on a base stair case potential. The squarewave has a frequency that is twice that of the staircase potential, and the current is sampled twice during each squarewave cycle; once at the end of the forward pulse and once at the end of the reverse pulse. By making the amplitude of the square wave large (25 to 50 mV), reverse pulses cause a reverse reaction to that of the forward pulses. Subtraction of the reverse current from the forward current yields current peaks at the redox potential of the analyte. Excellent sensitivity is obtained because the net current is larger than either the forward or reverse currents, charging current is minimized, and unwanted background currents are subtracted. Additionally, the scan rates are comparable to those of staircase voltammetry.

Alternating current (AC) voltammetry is slightly different than the techniques described above in the manner in which the charging current is minimized. The technique involves the superposition of a small-amplitude AC voltage on a linear ramp. Typically, the AC waveform has a frequency of 50–100 Hz and an amplitude of 10 mV. The AC component of the current is measured vs. the applied potential. Because the faradaic current is phase shifted by 45 degrees from the non-faradaic current, the charging current can be eliminated by the use of a phase sensitive current detector. The disadvantage of this technique is a substantial loss in sensitivity for reactions with slow electron transfer rates.

Stripping voltammetry is an electrochemical technique that offers excellent sensitivity by the addition of a preconcentration step to a standard voltammetric measurement. This technique is limited to analytes with high electron transfer rates and to analytes whose redox reaction by-products are solids or liquids. Anodic stripping voltammetry is used primarily for the determination of cations (e.g. $Cu^{2+}$, $Hg^{2+}$, $As^{3+}$) while cathodic stripping voltammetry is used for anions ($Cl^-$, $Br^-$). In anodic stripping voltammetry, a deposition potential, usually 0.3 to 0.5 V more negative than the redox potential, is applied to the working electrode for a sufficient time to allow for the analyte(s) to plate onto the sensing area, a period of time typically ranging from about 30 sec. to about 30 min. Those skilled in the art will appreciate how to determine the amount of time necessary for this pre-concentration (plating) step. During this time, ions are reduced at the electrode surface to form a solid or liquid. The amount of material plated onto the electrode surface is a function of both the deposition time and potential. After preconcentration, the potential is scanned in a positive direction using any of the waveforms listed above and the current is recorded. A 1000-fold increase in sensitivity over standard voltammetry is obtained due to the preconcentration step. In cathodic stripping voltammetry, the applied potential is 0.3 to 0.5 V more positive than the redox potential and, following preconcentration, the voltage is scanned in a negative direction. Cathodic stripping analysis is useful for determining anions that form salts at the surface of the electrode. Therefore, silver is a good choice for the determination of $Br^-$ and $Cl^-$ because the by-product of the redox reaction is AgCl or AgBr.

Additional variants of stripping voltammetry include potentiometric stripping analysis and adsorptive stripping voltammetry. In potentiometric stripping analysis, it is the potential vs. time that is measured following the preconcentration step. Analytes that have been concentrated on the surface are allowed to be oxidized chemically by oxidants that have been added to or occur naturally in the supporting electrolyte. The redox potential of the analytes measured will remain constant until all of the analyte has been oxidized back into solution. The resulting potential vs. time curve consists of a series of plateaus whose widths are a function of analyte and oxidant concentrations. A combined electrochemical-SPR (EC-SPR) measurement using the sensor device of the present invention and using potentiometric stripping analysis is extremely useful because the optical properties of the oxidation product can give information about naturally occurring oxidants in an unknown solution.

Adsorptive stripping voltammetry involves the formation, adsorptive accumulation, and reduction of a surface active complex of the metal. This technique usually involves a judicious choice of complexing agents to be added to the solution, and the response of the surface confined species is directly related to its surface concentration, with the adsorption isotherm providing the relationship between the surface and bulk concentrations of the adsorbate. The result is an extremely efficient method that can be used for low level detection of both inorganic and organic compounds. Because the technique relies on the addition of complexing agents, the number of measurable analytes is greatly increased as compared to previously discussed methods. From an EC-SPR standpoint, an electrochemical SPR measurement is extremely useful in the determination of appropriate complexing agents because these complexes should induce a change in the SPR portion of the signal.

Anodic-stripping voltammetry is described elsewhere in this disclosure. Cathodic-stripping voltammetry is analogous to anodic-stripping voltammetry, the difference being that initially a positive voltage is applied to the working electrode (SPR sensor in this invention), leading to oxidation of the analyte, whereby plating of the oxidized analyte occurs, followed by scanning the voltage in a negative direction to reduce the species off the sensor.

Amperometry involves voltammetric recordings at a fixed potential. This allows for detection of changes in currents as a function of concentration of redox-active species. Amperometry can be used to perform titrations and is very similar to voltammetry.

FIG. 1 depicts one embodiment of an SPR sensor of the present invention. FIG. 1 shows an SPR fiber sensor (1) constructed using a fiber optic with a glass core (2) and a plastic cladding layer (3). As specifically exemplified, the core diameter is 400 $\mu$m. Those of ordinary skill in the art recognize that the diameter of a fiber optic core is virtually limitless. However, at very large diameters, the modes essentially become continuous (and hence the sensor is a lightpipe). The fiber optic sensor is constructed by cutting an optical fiber, removing about 1 cm of plastic cladding from the tip (4) of the fiber, e.g., using hot sulfuric acid, and depositing a 3000 Å thick gold mirror (5) on the polished end of the fiber. The mirror (5) is deposited using an electron beam evaporator. The mirror is made thick enough so that it does not support SPR, e.g. about 1000 Å or more. A sensing area is provided around the outside of the exposed fiber by deposition of a 550 Å thick layer of gold (upon an adherence layer of chromium or titanium). The gold layer supports SPR. The 550 Å thick gold film, which provides the sensing area (6) that supports the SPW (wavy arrow) (8), is then evaporated onto the sides of the fiber optic using an electron beam evaporator. Electrical contact is made to the fiber optic SPR sensor by wrapping a 1 mil gold wire (7) around the base of the sensing area (6) of the sensor. The 300 nm gold mirror (5) does not support SPW and thus is not part of the "sensing area". When light is introduced into the fiber optic, it travels down the fiber optic via total internal reflection, hits the mirror and reflects off the mirror. The reflected light is then monitored to measure the SPR and electrochemical phenomena occurring at the sensing area (6).

Figure 2A:
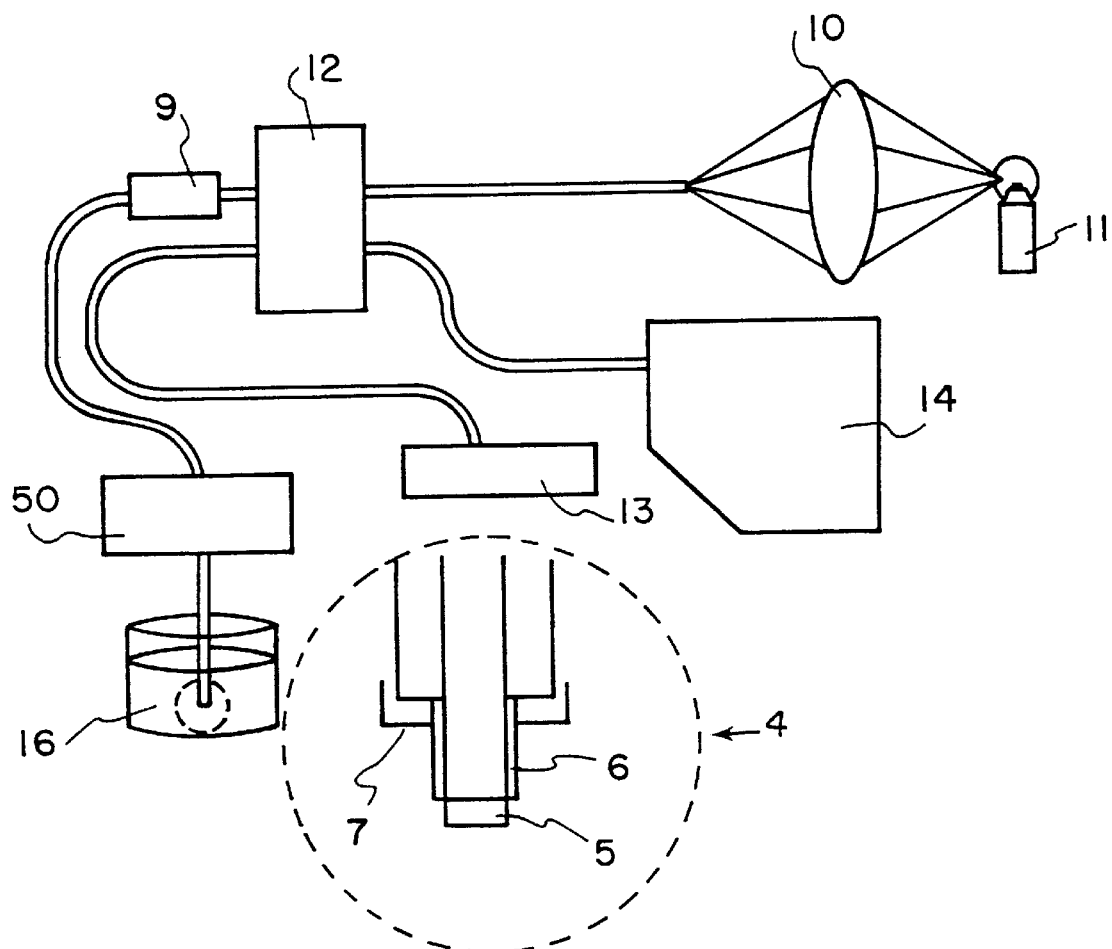
FIG. 2A is a schematic diagram of an experimental configuration of a sensor device wherein the sensor is a fiber optic. An expanded view of the tip of the sensor is shown. The sensor is connected to one arm of an optic splitter. The light is transmitted down the fiber optic to the sensing area whereupon the signal light is then reflected back up the fiber by the mirror at the end of the tip of the fiber optic. The returned light is split again and the output leg is connected to a fiber optic spectrograph which is used to measure the spectral intensity of the signal light. The voltage source, current meter and reference electrode are not shown.

FIG. 2A is a schematic diagram of an experimental configuration of a sensor device of this invention wherein the sensor is a fiber optic (1), the tip of which is submerged in a sample solution (16) containing analytes. An expanded view of the tip (4) of the sensor is shown. The sensor is connected to one arm of a fiber optic splitter (12). The sensor receives a portion, e.g. 50%, of the light which is coupled into the splitter using a lens (10) and a current controlled light source (11). In this embodiment, white light is used. A mode scrambler (50) is used to populate all the modes of the fiber optic. A connector (9) is used to connect the splitter to the (optionally disposable) fiber optic sensor. The light is transmitted down the fiber optic to the sensing area whereupon the signal light is then reflected back up the fiber by the mirror at the end of the tip. A narrow band of wavelengths are attenuated as a result of the SPR coupling of incident light to SPW at the metal dielectric (solution) interface. The returned light is split again and the output leg is connected to a fiber optic spectrograph (14) which is used to measure the spectral intensity of the signal light. The remaining arm of the splitter is index matched to a solution of glycerol in order to minimize back reflection and is transmitted to a beam dump (13). Electrical contact between the sensing area and the voltage source is provided by a wire (7). The voltage source, current meter and reference electrode are not shown.

Figure 2B:
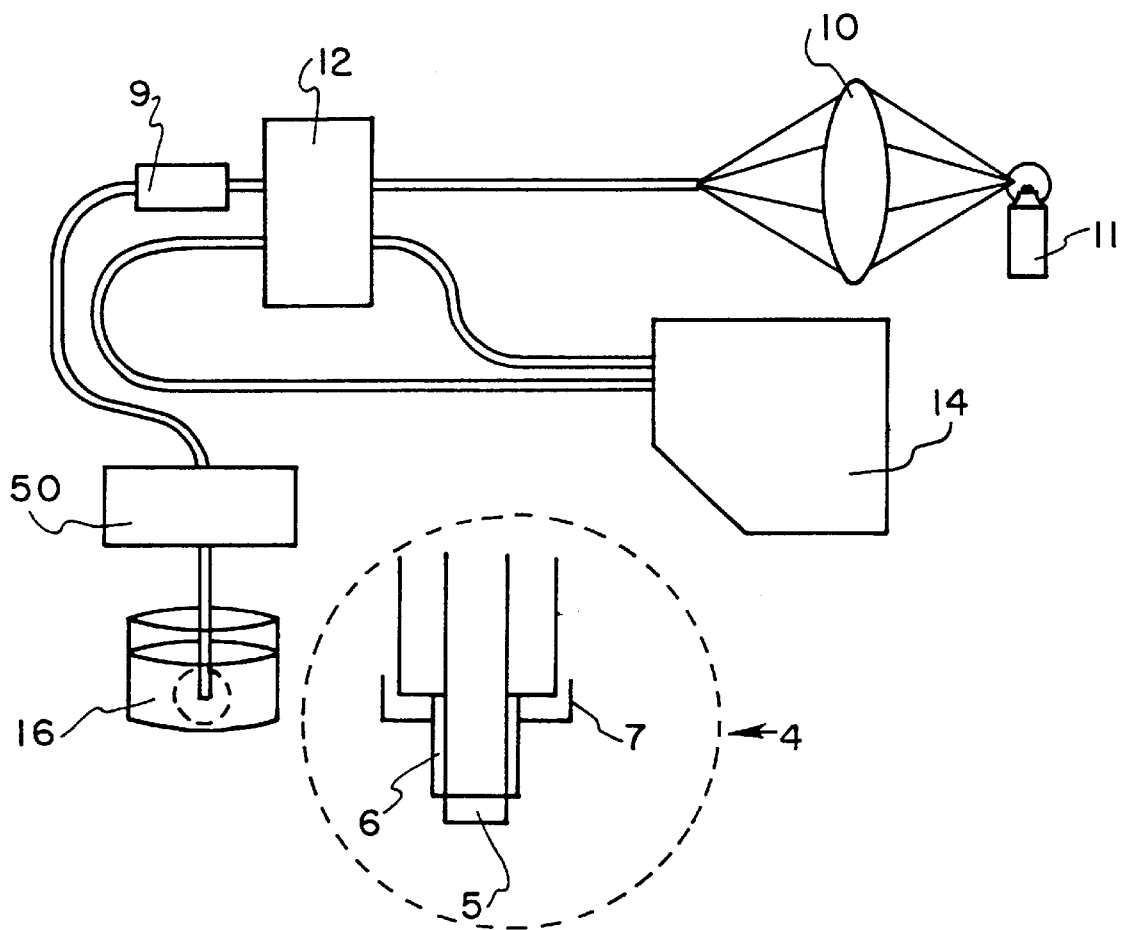
FIG. 2B is a schematic diagram of an experimental configuration of a sensor device wherein the sensor is a fiber optic. An expanded view of the tip of the sensor is shown. The sensor is connected to one arm of a fiber optic splitter. The light is transmitted down the fiber optic to the sensing area whereupon the signal light is then reflected back up the fiber by the mirror at the end of the tip of the fiber optic. The returned light is split again and the output leg is connected to a fiber optic spectrograph which is used to measure the spectral intensity of the signal light. The difference between the configuration in FIG. 2A

FIG. 2B is a schematic diagram of an experimental configuration of one of the sensor devices of this invention wherein the sensor is a fiber optic (1), the tip of which is submerged in sample solution (16) containing analytes. An expanded view of the tip (4) of the sensor is shown. The sensor is connected to one arm of a fiber optic splitter (12). The sensor receives a portion, e.g. 50%, of the light which is coupled into the splitter using a lens and a current controlled light source. In this embodiment, white light is used. A mode scrambler (50) is used to populate all the modes of the fiber optic. A connector (9) is used to connect the splitter to the (optionally disposable) fiber optic sensor. The light is transmitted down the fiber optic to the sensing area (6) whereupon the signal light is then reflected back up the fiber by the mirror at the end of the tip. A certain range of wavelengths are attenuated as a result of the SPR coupling of incident light to SPW at the metal dielectric (solution) interface. The returned light is split again and the output leg is connected to a fiber optic spectrograph (14) which is used to measure the spectral intensity of the signal light. The only difference between this configuration and the configuration in FIG. 2B is that a reference signal can also be measured by use of the remaining splitter arm. Electrical contact between the sensing area and the voltage source is provided by a wire (7). The voltage source, current meter and reference electrode are not shown.

Figure 2C:
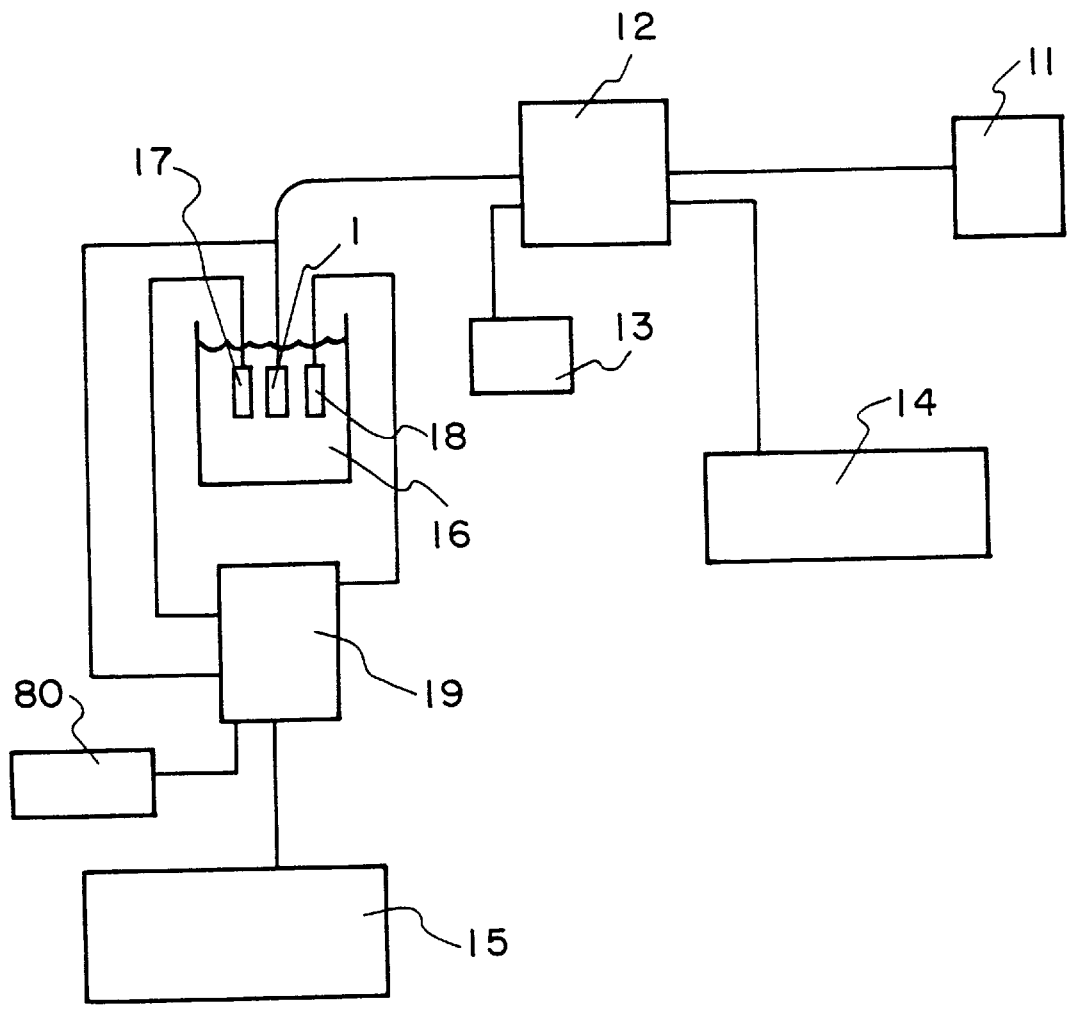
FIG. 2C is a schematic diagram of an experimental configuration of a sensor device showing a fiber optic and a splitter used to channel light into the wavelength detection system which detects the resonance minimum $\lambda_{sp}$, and a voltage source and current meter used to perform anodic stripping voltammetry.

FIG. 2C depicts another embodiment of the sensor device of the present invention using the sensor of FIG. 1. In the illustrated embodiment the wavelength modulation technique for SPR can be used. A broad band light source, e.g. white light, (11) is coupled via splitter (12) into the fiber optic sensor (1). Light at the proper wavelength $\lambda_{sp}$ to satisfy the resonance condition given by Eq. (1), results in the excitation of an SPW on the 550 Å thick gold film of the sensing area. Some energy in the light at the resonance wavelength is absorbed by the excitation of the SPW. This results in a dip in the intensity spectrum of light reflected by the SPR fiber sensor. A splitter (12) is used to channel reflected light into a device (14) which detects light intensity as a function of wavelength, e.g. a spectrometer or filters and photodetectors. A beam dump (13) allows for removal of the extra leg of light. By monitoring the resonance wavelength $\lambda_{sp}$ at which the SPR occurs (the surface plasmon resonance signal), the effective index of refraction of the solution surrounding the fiber optic sensor can be determined. This resonance dip in the reflected light intensity can be modeled using Fresnel's reflection matrices (Ishimaru, A. (1991), *Electromagnetic Wave Propagation, Radiation, and Scattering,* Prentice-Hall, New Jersey, pp. 43–45).

When an electrical potential is applied by a voltage source (15), to the gold film on the fiber optic sensor (1) that supports the SPW, ions in a sample solution (16) can be reduced or oxidized on the sensing area (6). An optional potentiostat (19) allows for the measurement of the electrical potential between the reference electrode (17) and the sensing area (working chemical electrode) (6) of the SPR sensor with minimum loss due to solution resistance. By monitoring the resonance wavelength $\lambda_{sp}$, it is possible to detect the thickness of the plated layer and the flux of redox-active analytes to and from the sensing surface. A current meter (80) measures the electrical current.

A preferred embodiment of the device of this invention is one in which the sensor device is miniaturized. That is, it is preferred that the sensor device be small, to enhance sensitivity. A preferred embodiment is a miniature or integrated configuration which reduces the dimensions of the sensing area preferably to a size which is much less than the diffusion length of the analyte to be measured (typically less than 25 $\mu$m). The reduced dimensions offer several benefits including a reduced surface area which corresponds to a reduced diffusion layer capacitance. This means higher scan rates during a measurement. Another benefit to reduced sensor dimensions is a higher flux of analyte to and from the surface during a measurement. This effect is defined in terms of a mass-transport rate constant, $k_D$, which is the ratio of the diffusion coefficient of the analyte to the smallest dimension of the sensor surface and has units of m/s. Therefore, $k_D$ has units of velocity and it defines the speed at which an analyte gets to and from the sensor. Since $k_D$ is inversely proportional to the smallest dimension of the sensor surface, smaller sensors mean higher flux and, consequently, a shorter pre-concentration time during a stripping voltammetry experiment. A miniature sensor configuration is also preferred because it allows the sensor to be made in an inexpensive manner which allows the sensing element to be disposed of after a measurement has been made. This is important because these electrodes do not last, and there is not a practical way to polish the very thin SPR supporting films without damaging them or changing their thicknesses.

Figure 3:
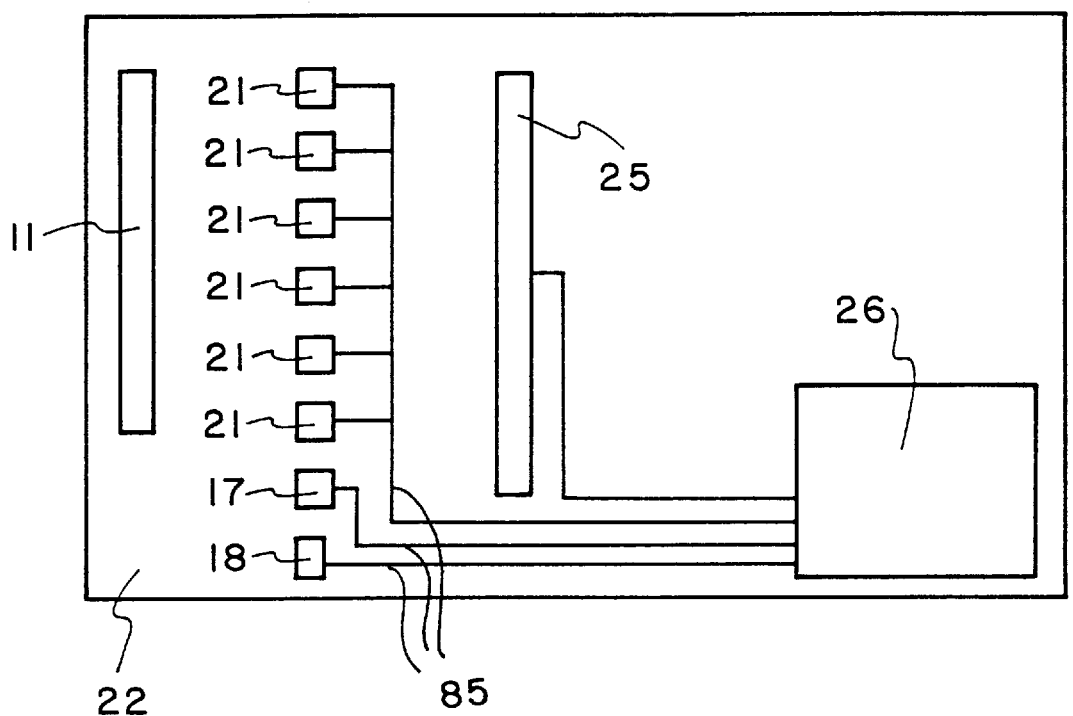
FIG. 3 is a top view schematic diagram of an experimental configuration of a sensor device of this invention showing SPR sensors in an integrated configuration. The light source, voltage source, current meter, photodetectors, and all of the signal processing may be included on a chip.

A preferred embodiment, therefore, is in an integrated optical configuration. Integrated configurations include those configurations in which at least some of the optics necessary to generate the SPR signal are combined on an integrated circuit chip. (These optics include a sensor and optical components necessary to bring light to the sensor and take light from the sensor.) Integrated configurations also include those configurations wherein any of a light source, voltage source, current meter, and/or signal processing are combined on the IC chip, in addition to the SPR sensor and its input and output optics. Chemical electrode performance can be enhanced by reducing the surface area of the sensor. One design for such an integrated sensor is shown in FIG. 3. This design encompasses several SPR sensors (chemical electrodes) (21) on a single integrated circuit (IC)(22) which may be, among others, a silicon wafer. The SPR sensors can be made out of different conducting materials (for instance nickle, copper, chrome, platinum, palladium, and alloys thereof) to enhance selectivity, or several similar sensors can be placed side-by-side for redundancy. The light sources (11) optically couple light to the SPR sensors (chemical electrodes) (21). The light is then analyzed by an optical signal detector (25). The signal processing, voltage source, and ammeter are indicated by (26), all of which are illustrated on chip. The currents as a function of applied potential are measured with an ammeter (26). Strip lines (85) electrically connect the sensors to the voltage source, signal processing and ammeter, all of which are indicated by (26). A reference electrode (17) and auxiliary electrode (18) allow for the desired potential at the sensing area of the sensors (21). One or more of the sensors (21) could be left unconnected to the voltage source and thereby monitor only SPR.

The exact positions of the reference electrode (17) and auxiliary electrode (18), as well as the voltage source and current meter, relative to the other elements of the device are not critical and can be positioned differently than the depiction in the figures of this disclosure. Those skilled in the art will appreciate that the reference electrodes which can be used in the device and methods of this invention are isolated with an ion barrier of some kind (such as a salt bridge to a separate container) or a membrane surrounding the reference electrode if it is in the same container or flow cell as the working electrode. In FIG. 3 the reference electrode (17) is shown as a small square the same size as one of the SPR sensors. However, it could be placed anywhere on the IC and be any size, or several reference electrodes could be fabricated at strategic locations around the IC. The IC could also provide some kind of interface (not shown in FIG. 3) which could be used to connect the sensor with a display or a personal computer (PC).

Figure 4:
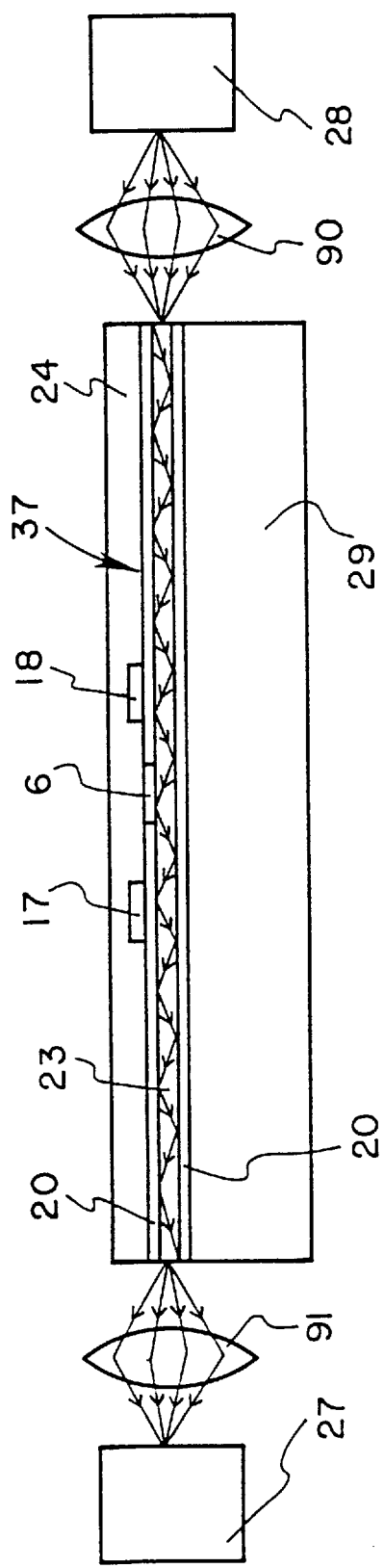
FIG. 4 is a side view of another embodiment of the integrated configuration wherein a reference and auxiliary electrodes are positioned on the cladding of the waveguide and the waveguide is integrated into a substrate.

FIG. 4 is a side view of a different embodiment of an integrated waveguide. FIG. 4 depicts a wavelength modulation configuration. Multimode waveguides are fabricated on top of the substrate (29), which in this embodiment is an integrated circuit chip. The IC chip (substrate) (29) can be made of silicon, GaAs or some other semiconductor, or glass, pyrex, plastic, or essentially any other planar material could be used as a substrate. A broad band light source (28), e.g. white light, is coupled into the waveguide (37) via a means (90) for coupling light into an SPR sensor. Means (26) for coupling light into an SPR sensor include, but are not limited to, a lens, a lens system, prism coupler, or a grating. Means (90) for coupling light depends on the sensor configuration. A small section of cladding (20) on each waveguide is removed and the conducting film which supports SPR is fabricated in this area (6). The film can be fabricated in this area by various means, including but not limited to, thermal evaporation, electron-beam evaporation, DC sputtering, RF sputtering, or DC magnetron sputtering. As the light travels down the core (23) of the waveguide (37), it excites an SPW at the surface of the conducting film (sensing area) (6). Means (91) for coupling light out of the waveguide and into a detector (27) which detects the intensity of light as a function of wavelength is provided. The light exiting the sensor contains the surface plasmon resonance signal. The detector (27) can be a grating and an array detector to determine at which wavelength the SPR is occurring. Means (91) for coupling light out of the SPR sensor include, but are not limited to, a lens, a lens system, prism coupler, butt coupler or a grating. A flow cell (24) containing redox-active analytes in solution is shown above the waveguide. Reference electrode (17) and auxiliary electrode (18) are also shown. The position of these electrodes relative to the sensing area (6) can be different from those shown and determined by one of ordinary skill in the art.

The sensor device illustrated in FIG. 4 could be adapted to perform angle modulation. In this case, the light source would be monochromatic and the detector an angle detection device (such as a photodetector array). Rays with multiple angles of propagation would propagate down the waveguide.

Figure 5:
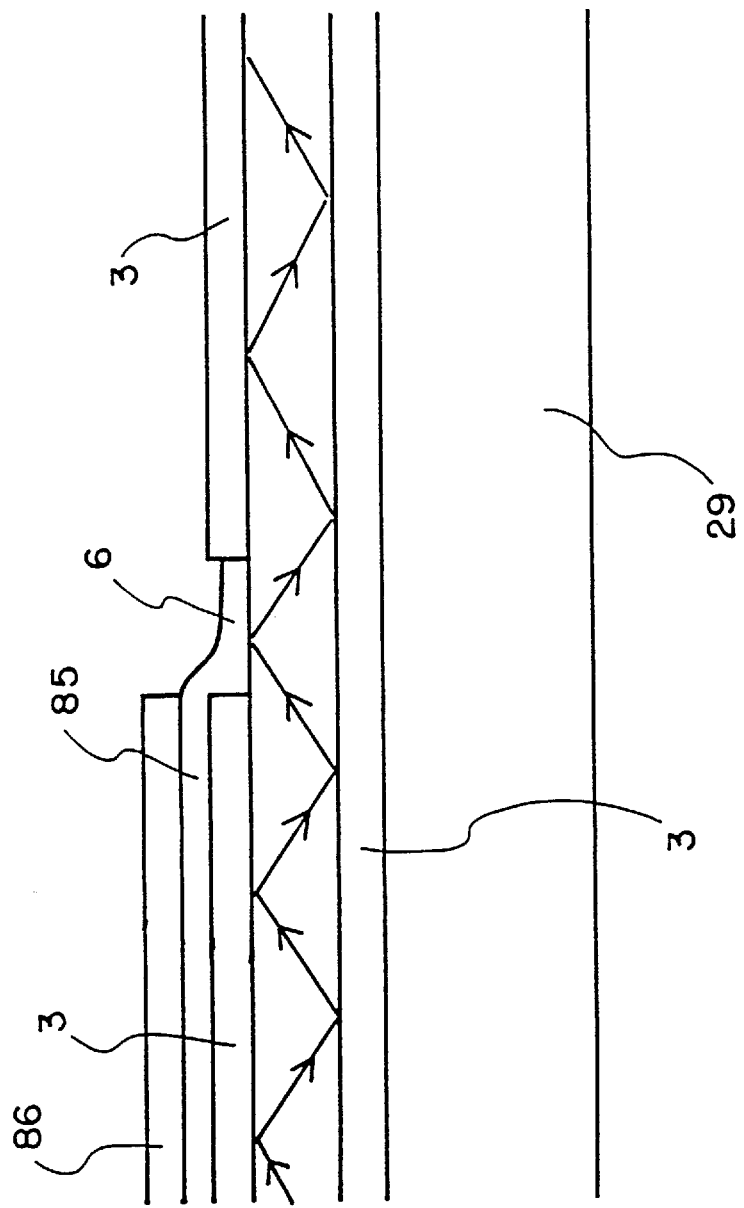
FIG. 5 is a cross section of a waveguide sensor of the present invention showing the strip lines which make electrical contact between the sensing area and the voltage source, current meter (ammeter) and signal processing. The strip lines are over-coated with insulating material (e.g. $SiO_2$).

The chemical electrode measurement is made by contacting the conducting film on the IC with strip lines (85), as shown in FIGS. 3 and 5. These lines are over-coated with an insulating material (86), such as $SiO_2$. The lines are connected to the signal processing circuitry, which may be integrated on the same substrate. This circuitry provides the current measurements as it sweeps the voltage across the conducting films.

In the integrated configuration, the light sources and signal processing (detection devices, voltage source and current meters or other voltage sources and current meters) could be integrated all on the same IC. On the other hand, the signal processing can be done off chip.

Figure 6:
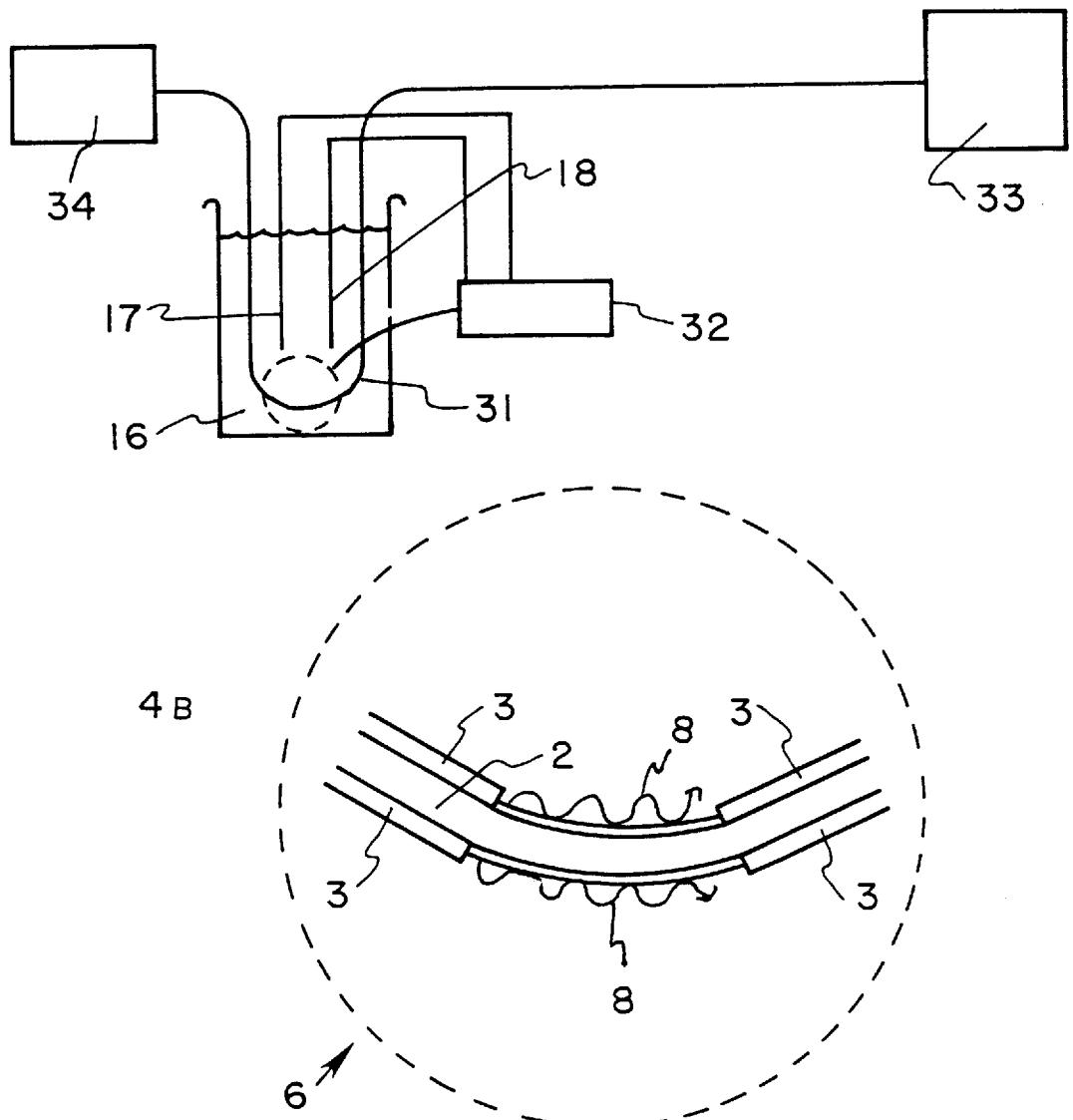
FIG. 6 is a side view schematic diagram of another embodiment of the sensor device of the present invention. The SPR sensor is a fiber optic. A container holds a solution of polarizable, ionic or redox-active analytes. Also in the container is the fiber optic which is U-shaped. Near the bottom of the "U" is the sensing area, which is shown in an expanded view. The wavy arrows represent the SPW. Also in the container are an auxiliary electrode and a reference electrode, both of which, in addition to the fiber optic SPR sensor, are connected to a voltage source and current meter. A light source and detection device are also shown.

FIG. 6 is a side view schematic diagram of another embodiment of the sensor device of this invention. The SPR sensor (31) comprises a fiber optic. A container holds a sample (16) of redox-active analytes. Also in the container is the fiber optic (31) which is U-shaped. The fiber does not have to be U-shaped. For example, it could be put inside a capillary tube which would be used essentially as a flow cell, in which case the fiber could remain straight. Or it could be bent in any configuration which does not exceed the maximum bend radius of the fiber, which is typically about one inch. Near the bottom of the "U" is the sensing area (6), which is shown in an expanded view. Cladding is removed to allow for the sensing area. Preferably about 1 cm of cladding is removed. However, 0.1 cm to a few cm can be removed from a fiber optic whose core diameter is about 400 $\mu$m. Those skilled in the art recognize that the amount of cladding removed depends on the diameter of the fiber optic. Also in the container are an auxiliary electrode (18) and a reference electrode (17), both of which, in addition to the fiber optic SPR sensor, are connected to a voltage source and current meter (32). A light source (33) and detector (34) are also shown. This embodiment could be performed with the wavelength modulation, angle modulation or phase modulation techniques. Hence the light source (33) could be either monochromatic or broad band, and the detection device (34) could be either an angle detection device or a wavelength detection device, respectively, as described above.

The fiber optic SPR sensor in FIGS. 2A, 2B, 2C and 6 have a larger surface area compared to the waveguides in the integrated configurations in FIGS. 3 and 4. The larger surface area effects a longer time for preconcentration of analyte since the dimensions of the electrode are inversely proportional to the mass-transport rate of analyte to the electrode surface. A large surface area also causes a larger diffusion layer capacitance which leads to slower scan rates.

In general, sensors of this invention based on spherical, hemispherical, or cylindrical geometries are preferred to planar sensors. This arises from considerations regarding analyte flux uniformity at the surface of the EC-SPR electrode which is strongly dependent on sensor geometry. The radial symmetry provided by spherical, hemispherical, or cylindrical geometries insures a uniform flux of analyte across the surface of the sensor. Since the SPR portion of the signal is measuring light intensity at the surface, a non-uniform distribution of analyte across the sensor surface can lead to inaccurate measurements. In the case of planar sensors, (disk or rectangular geometries), the flux of analyte is non-uniform and occurs primarily at the edges of these structures. This non-uniform flux is enhanced as the dimensions of the active area of the sensor are decreased. In the worst case, this means that a large portion of the active area of an EC-SPR sensor may be completely devoid of analyte during a stripping voltammetry experiment. This could severely hinder the ability of the sensor to measure the optical properties of the analyte at the surface. (R. M. Wightman and D. O. Wipf "Voltammetry at ultramicroelectrodes," Electroanalytical Chemistry 15 (1989) p. 267.) However, it is possible to calibrate a sensor even if the flux is non-uniform and obtain quite good results.

Figure 7A:
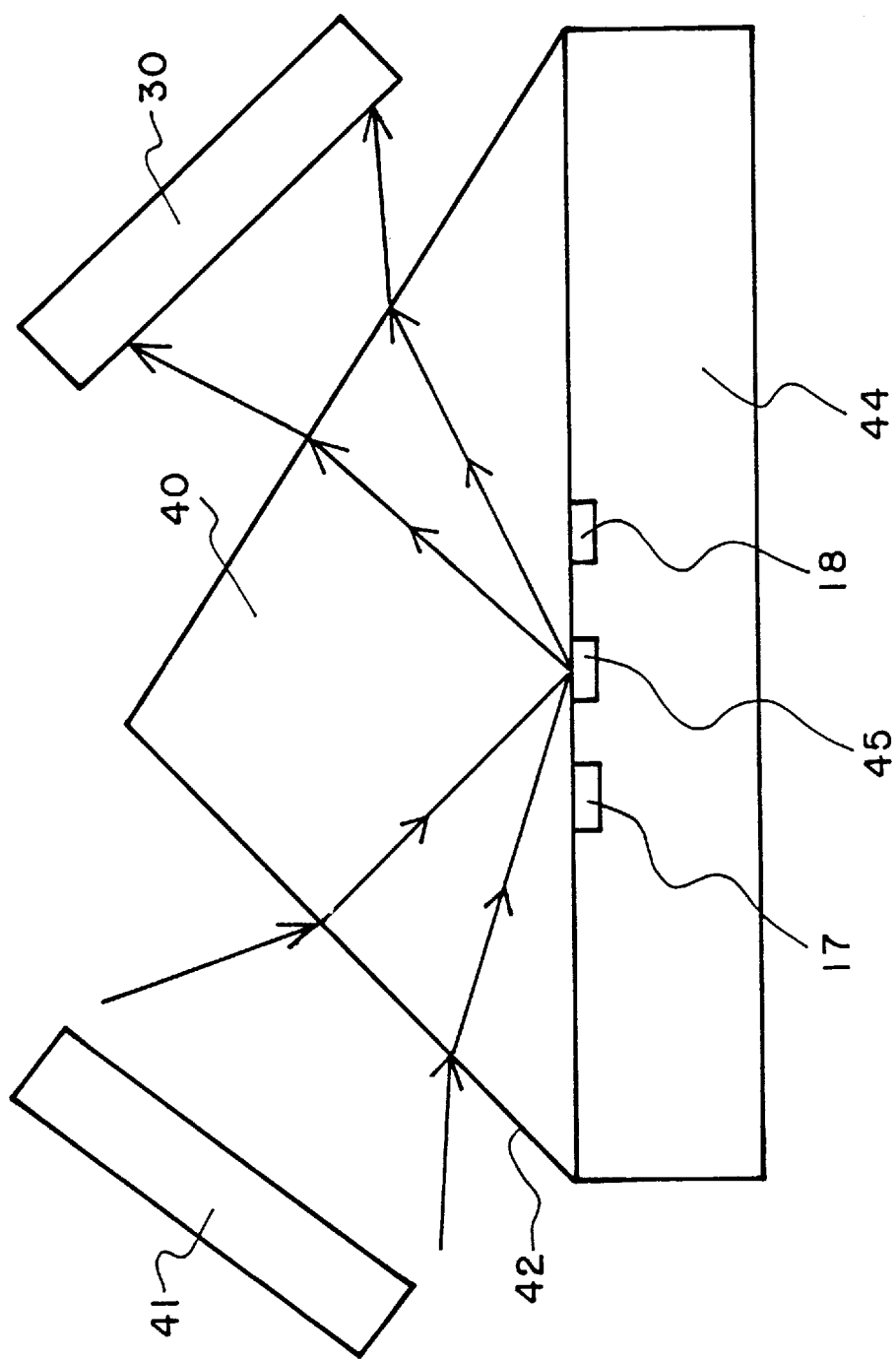
FIG. 7A is a schematic diagram of a configuration of a sensor device of the present invention showing an SPR sensor using the Kretschmann configuration comprising a prism with a flow cell attached to the bottom. To adapt the Kretschmann configuration to the device of the present invention, a reference electrode and an auxiliary electrode are included in the configuration. The sensing area and other electrodes are represented as rectangles. A source of monochromatic light is shown, as well as a means for detecting the intensity of the reflected light as a function of angle of incidence. Voltage source and current meter are not shown.

FIG. 7A shows an adaptation of a conventional SPR configuration for use as a sensor device of the present invention, a bulk optic configuration using a prism. In this method either the angle modulation or the wavelength modulation techniques can be used to excite SPR. FIG. 7A depicts angle modulation. A monochromatic light source (41) is positioned so that a range of angles of light is directed onto a side (42) of a prism (40). A layer of conducting film is deposited in an area of the base of the prism, forming the sensing area (45). The base of the prism must be in contact with a sample solution. For example, a flow cell (44) can be attached to the base of the prism, or the base of the prism can be submerged into sample. The incident light, minus the light which is coupled to the SPR, reflects off the conducting film at the sensing area (45) and is detected by a device for detecting intensity of light as a function of angle (30). Reference electrode (17) and auxiliary electrode (18) are shown. A voltage source and current meter are not shown. Due to the large size of a bulk optic SPR sensor, the device will have the same limitations as the fiber optic SPR sensor, in terms of the chemical electrode sensing.

Figure 7B:
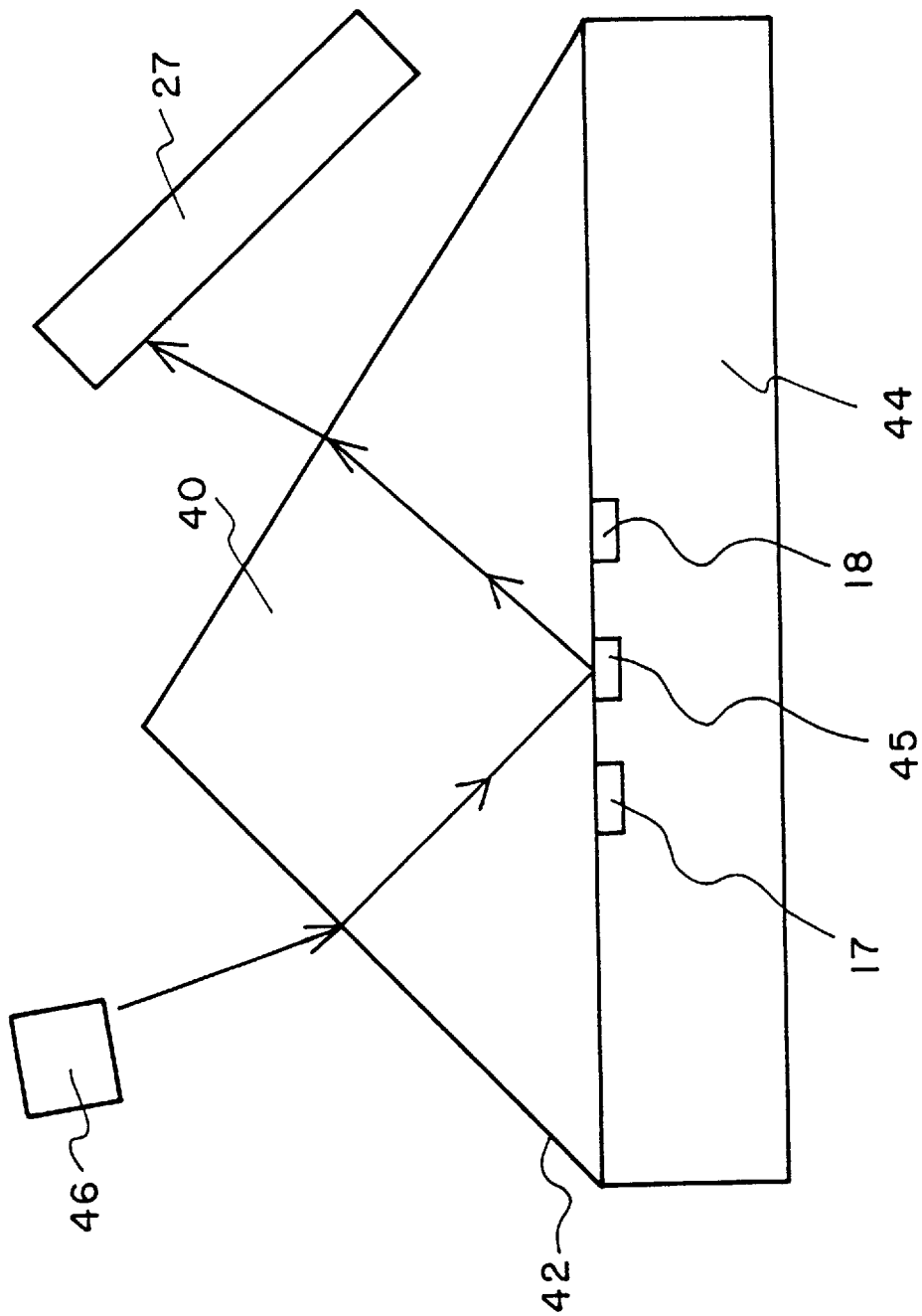
FIG. 7B is a schematic diagram of a configuration of one of the sensor devices of the present invention showing an SPR sensor using the Kretschmann configuration comprising a prism with a flow cell attached to the bottom. To adapt the Kretschmann configuration to the device of the present invention, a reference electrode and an auxiliary electrode are included in the configuration. The sensing area and other electrodes are represented as rectangles. A source of broad band light is shown, as well as a means for detecting the intensity of the reflected light as a function of wavelength. Voltage source and current meter are not shown.

FIG. 7B shows a bulk optic SPR configuration using a prism with wavelength modulation. A broad band light source (46) is positioned so that light at a single angle is directed onto a side (42) of a prism (40). A sensing layer of conducting film is deposited in an area of the base of the prism, forming the sensing area (45). The base of the prism must be in contact with sample solution, for example by use of a flow cell (44) attached to the base of the prism. The incident light, minus the light which is coupled to the SPR, reflects off the conducting film at the sensing area (45) and is detected by a device for detecting intensity of light as a function of wavelength (27). Reference electrode (17) and auxiliary electrode (18) are shown. A voltage source and current meter are not shown. Due to the large size of a bulk optic SPR sensor, the device will have the same limitations as the fiber optic SPR sensor, in terms of the chemical electrode sensing.

Any SPR sensor configuration can be used to implement the SPR chemical electrode sensor of the present device. For example, by combining both the angle modulation and the wavelength modulation techniques in one sensor, it is possible to sense the dispersive index of refraction of an unknown solution.

Figure 8:
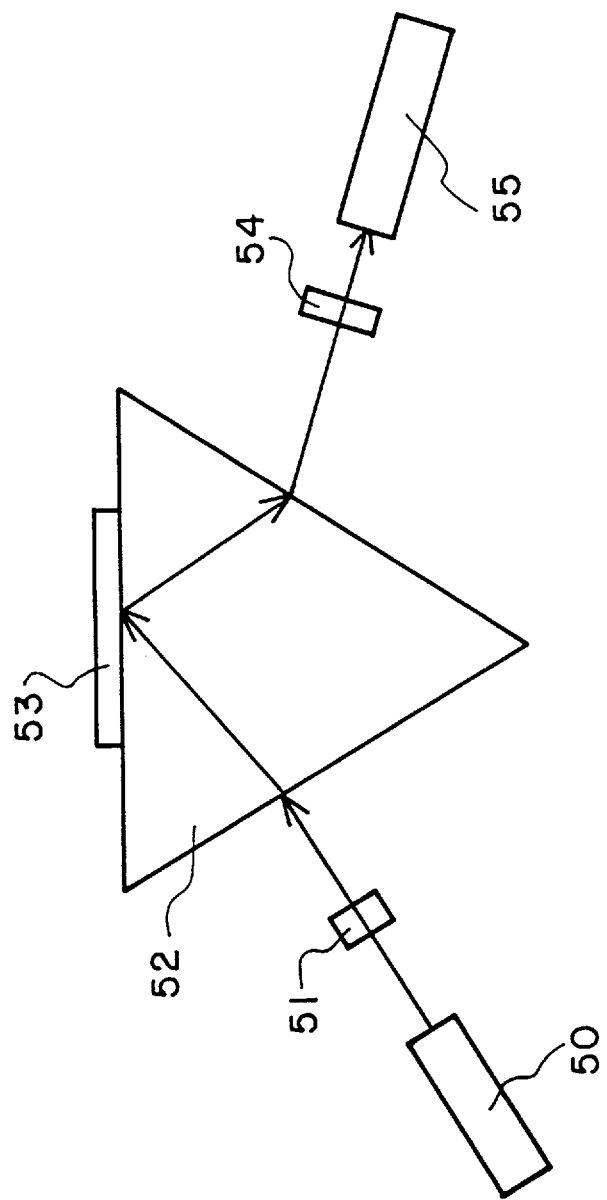
FIG. 8 is a schematic diagram of one embodiment of the present invention which uses phase modulation.

Phase modulation techniques can also be used in the device of the present invention. This configuration is illustrated in FIG. 8. It uses a source of randomly polarized light, e.g. a randomly polarized laser, a compensator for adjusting the phase angle of the incident light, a polarizer, and a detector. The compensator is adjusted so that the maximum amount of light gets through the polarizer at the physical angle at which SPR occurs. After the phase angle has been adjusted with the compensator, the sensor is operated by changing the physical angle of incidence of the light while measuring the optical intensity of the reflected light. Any change in RI that is within the range of the SPW will cause the phase of the TM component of the reflected light to change. This will be manifested in a change in the intensity as a function of the physical angle of the photodetector.

In the phase modulation SPR configuration, the TM-polarized component loses some intensity to the resonance phenomenon. However, the resultant polarization of the reflected beam has a component which is transmitted through the analyzer and which hits the detector. This signal increases until the phase change of the TM-polarized component is $\pi$ at $\theta_{sp}$.

FIG. 8 illustrates a sensor device of the present invention using the phase modulation configuration. A laser (50) is the source of electromagnetic radiation (which contains both TM- and TE-components). A compensator (51) corrects differences in phase shifts of the TM- and TE-components. Light is coupled into the prism (52) which includes a layer of conducting metal (53), thereby inducing an SPW. Reflected light is transmitted to a polarizer (54) which is positioned between the prism and the detector (55) so that at non-resonant angles, little or no light is transmitted to the detector.

Figure 9:
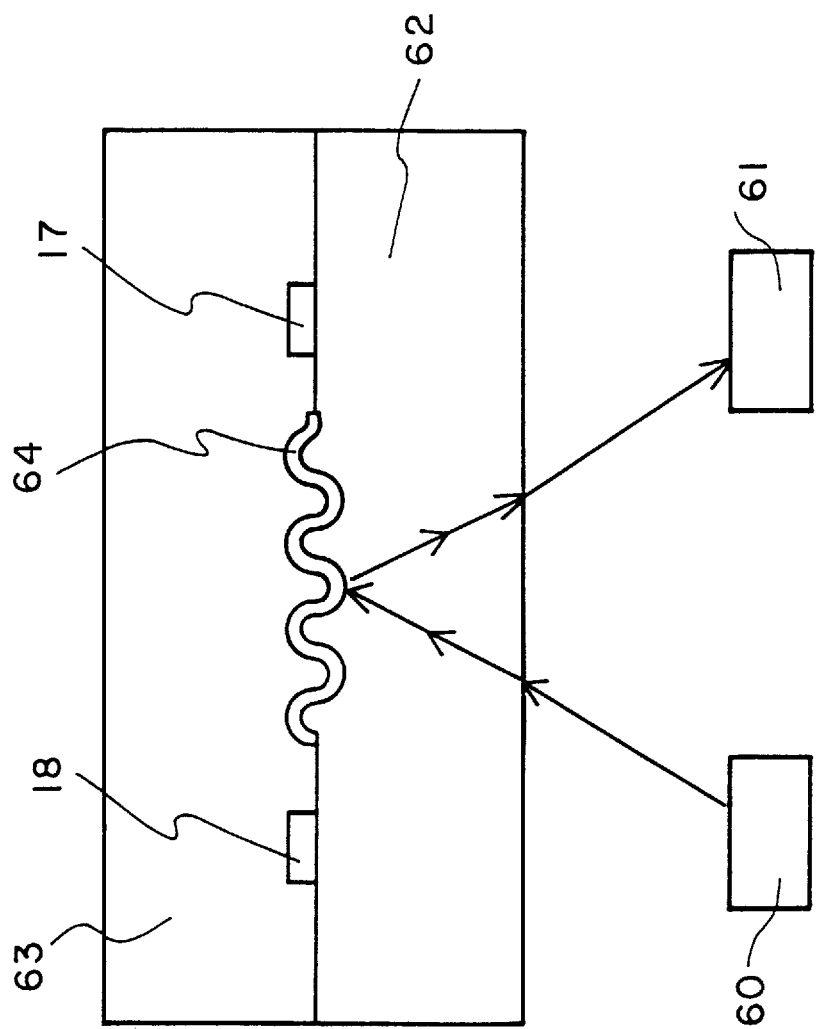
FIG. 9 is a schematic diagram of one embodiment of the present invention using a grating as the sensing area. The grating is fabricated on a transparent material, e.g. the base of a prism, a section of light pipe, the core of a waveguide, or simply a planar substrate.

FIG. 9 is a schematic diagram of one embodiment of the present invention using a grating as the sensing area. The grating (64) is fabricated on a transparent material (62), e.g. the base of a prism, a section of light pipe, or simply a planar substrate. A flow cell (63) contains the grating (64) (sensor), as well as reference electrode (17), (optional) auxiliary electrode (18), and solution containing redox-active analytes. Light is transmitted from a light source (60) to the grating (64), resulting in an SPW. The reflected light is measured by a detector (61). The electric current is also measured. The voltage source and current meter are not shown.

Figure 10:
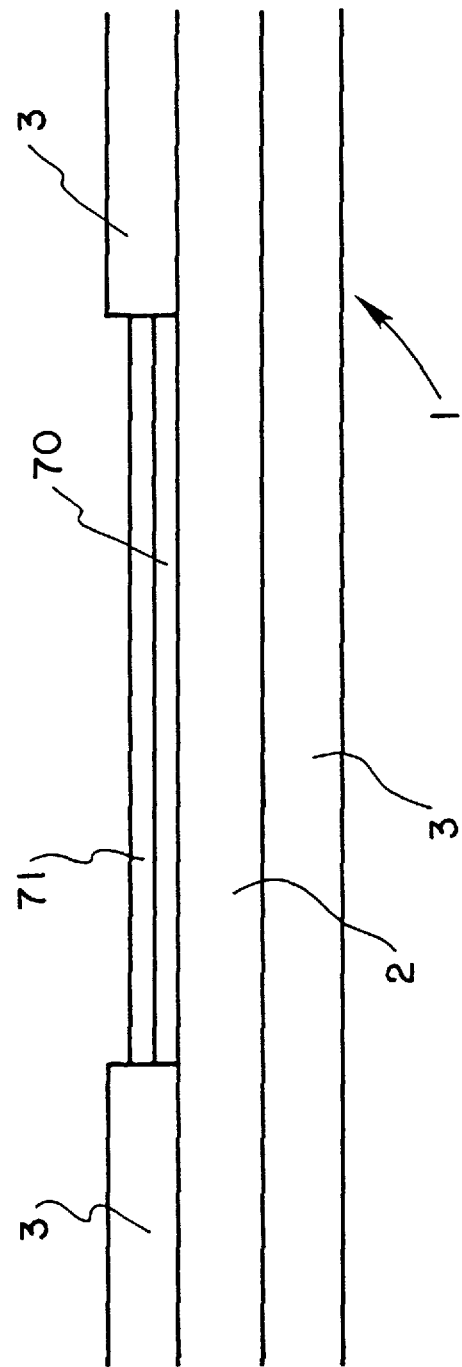
FIG. 10 is a schematic diagram of one embodiment of the present invention using a fiber optic (1) which supports long range SPR.

Long range surface plasmons (LRSP) in any configuration which supports SPR can also be used. LRSP is two SPWs excited on the top and bottom layers of a thin conducting film. FIG. 10 is a schematic diagram of one embodiment of the present invention using a fiber optic (1) which supports long range SPR. The core (2) of the fiber optic is covered with cladding (3), which is removed in part to allow for coating part of the core with a dielectric material (70) with a lower refractive index than that of the core (2). Covering this dielectric material (70) is a thin layer of material (71) which supports long range SPR. This material (71) could be, for instance, a 200 Å layer of gold.

In addition to the device of the present invention, methods for detecting and identifying unknown analytes are also disclosed in the present invention/application. A method for detecting analytes in a sample includes the steps of:

(a) contacting the sample with the sensing area of a surface plasmon resonance sensor;(b) introducing electromagnetic radiation into the surface plasmon resonance sensor;(c) applying a voltage, for a sufficient time to allow for an analyte to be adsorbed or plated onto the sensing area, to the sensing area of the sensor and optionally to a reference electrode and an auxiliary electrode;(d) measuring the surface plasmon resonance signal exiting the surface plasmon resonance sensor, optionally as a function of applied voltage; (e) optionally measuring the current across the sensing area of the sensor as a function of applied voltage.

The teachings of this disclosure demonstrate that it is possible to selectively detect redox-active analytes in solution using electrochemical techniques with an SPR sensor. The SPR sensor has an advantage over standard electrochemical sensors, because the signal is detected optically rather than by measuring a current, as is done with conventional chemical electrodes. This eliminates the unavoidable measurement problem which plagues standard chemical electrodes, that of separating the background currents due to charging processes from the primary Faradaic current of interest. Unlike standard electrochemical techniques, the SPR sensor is also sensitive to the binding of neutral particles which may occur at the surface. Another advantage of the sensor device of this invention is that it provides for a single sensor to detect both redox-inactive and redox-active species, which can be useful in situations where space is limited, e.g. in vivo or microscale experiments.

U.S. Pat. Nos. 5,374,563; 5,067,788; 4,844,613; 5,035,863; 4,997,278; 5,064,619; 5,055,265; 5,478,755; 5,047,213; 5,313,264; 5,327,225; 5,485,277; U.S. provisional application Nos. 60/005,878, 60/007,027, 60/009,169 and corresponding U.S. applications (attorney docket no. 89-95, 89A-95, and 101-95, respectively) filed Oct. 25, 1996; Jorgenson, R. C. and Yee, S. S. (1993), "A fiber optic chemical sensor based on surface plasmon resonance," Sensors and Actuators B 12:213–220; Jorgenson, R. C. and Yee, S. S. (1994), "Control of the dynamic range and sensitivity of a surface plasmon resonance based fiber optic sensor," Sensors and Actuators A 43:44–48; Jorgenson, R. C. et al., U.S. Pat. No. 5,359,681, as well as all other references cited in this specification, are incorporated in their entirety by reference herein.

The following example is provided for illustrative purposes, and is not intended to limit the scope of the invention as claimed herein. Any variations in the exemplified devices and/or methods which occur to the skilled artisan are intended to fall within the scope of the present invention.

EXAMPLE

A fiber optic SPR sensor of the type illustrated in FIG. 1 was placed in a beaker of 0.05M acetate buffer with a pH of 5.0. Only the 1 cm long active tip of the sensor was submerged in solution. A silver/silver chloride reference electrode was also placed in the solution. The buffer solution was deoxygenated by bubbling gas into it for fifteen minutes. The nitrogen was then positioned so that a constant stream of $N_2$ gas flowed over the surface of the beaker. Solutions containing $Pb^{2+}$ and $Cu^{2+}$ cations were added to the beaker, so that a total concentration of 10 ppm $Cu^{2+}$, and 13.76 ppm $Pb^{2+}$ was present in the beaker.

The metal ions are electroplated onto the surface of the SPR sensing area and then electrically stripped off. The current which flows during the stripping process is proportional to the metal concentration, and the voltage at which the stripping occurs corresponds to the type of metal in the reaction. The standard reduction potentials for the metal cations in this experiment are as follows:

$$Cu^{2+}+2e^-<=>Cu \quad E^0=0.3419 \text{ V}$$

$$Pb^{2+}+2e^-<=>Pb \quad E^0=-0.1262 \text{ V}$$

where $E^0$ is measured under specific conditions and with respect to a normal hydrogen electrode (NHE). To convert to potentials relative to the Ag/AgCl reference electrode used, one must subtract 0.199V:

$$E^0{}_{Cu}=0.141 \text{ V}, E^0{}_{Pb}=-0.325 \text{ V (vs. Ag/AgCl)}$$

These are standard reduction potentials. The actual reduction potentials for these metals differ in acetate buffer solution. (Kh. Z. Brainina, *Stripping Voltammetry in Chemical Analysis* (1974) NY: John Wiley & Sons.)

Figure 11A:
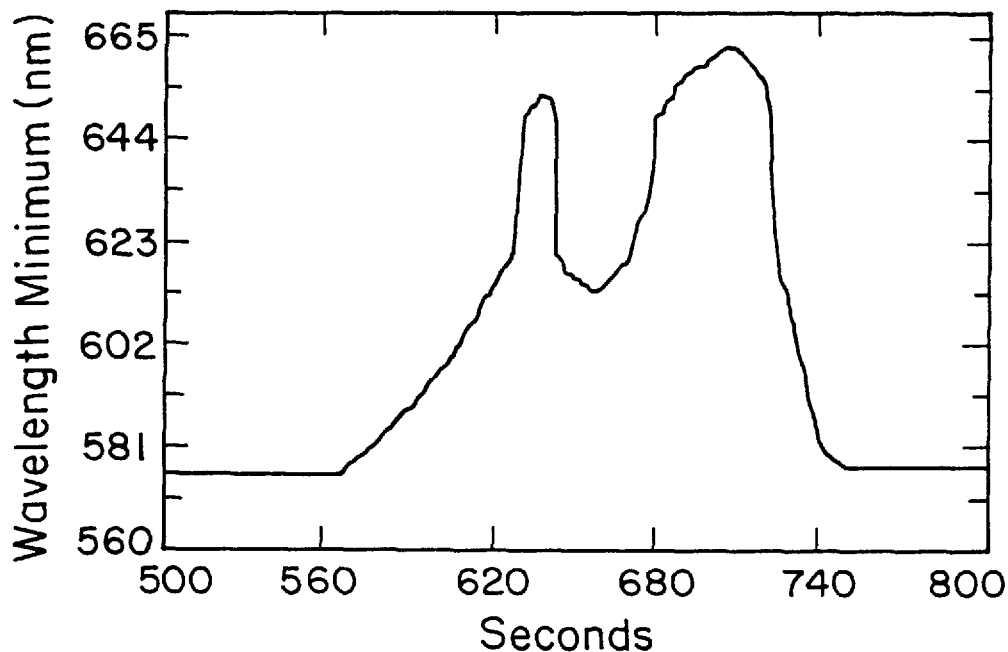
FIG. 11A is a graph of the resonance minimum $\lambda_{sp}$ as a function of time, for the experiment in which lead and copper cations were reduced to metals and then oxidized back to cations. The configuration used was similar to that in FIG. 2C except that no auxiliary electrode or potentiostat was used.
Figure 11B:
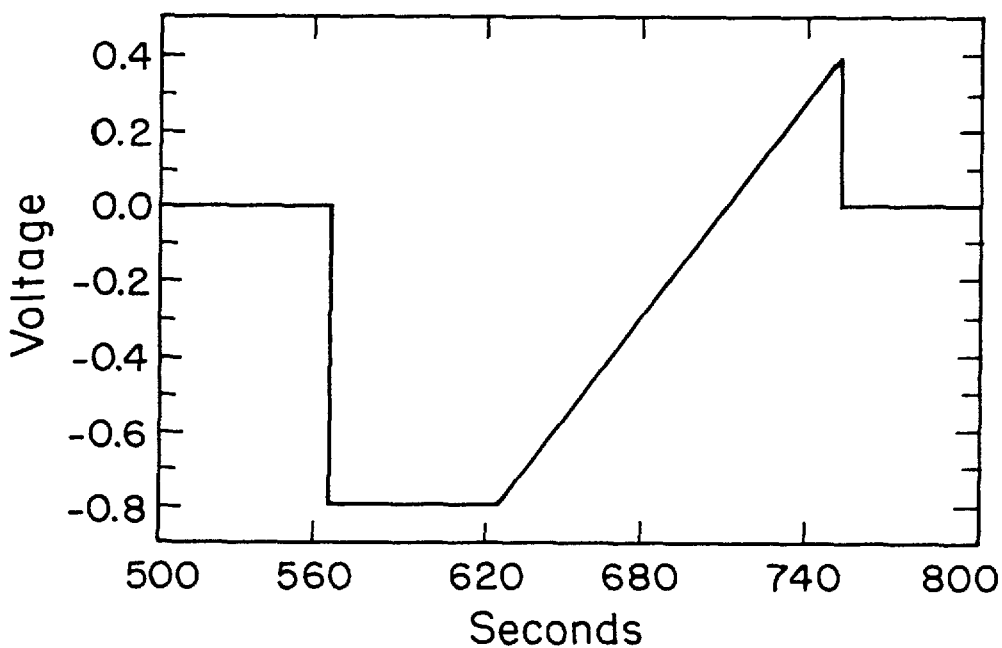
FIG. 11B is a graph of the voltage applied to the SPR sensor as a function of time, for the experiment described in FIG. 11A.

After establishing a baseline, the data shown in FIG. 11A and 11B were taken. FIG. 11B shows the potential applied to the electrode as a function of time. FIG. 11A shows the resulting change in the SPR wavelength minimum $\lambda_{sp}$. The voltage was initially held at zero volts while a baseline was established. Then at 564 seconds the voltage was set to −0.8 V for 60 seconds. This causes reduction of both $Cu^{2+}$ and $Pb^{2+}$ cations, resulting in plating of the elemental metals onto the gold surface of the SPR sensor. This plating of Cu and Pb metal onto the surface causes a change in the effective index of refraction. This is evident in FIG. 11A, as the $\lambda_{sp}$ starts to climb from its initial value of 575 nm. At the end of sixty seconds, the voltage increases from −0.8 V to 0.4 V at the rate of one 10 mV step every second. Both the Cu and Pb cations continued to be reduced at the surface of the gold until the voltage reaches the Nernst oxidation potential for Pb, at −0.427 V with respect to the Ag/AgCl reference electrode at 0.199 V in the 0.05M acetate buffer solution. [Heyrovsky, J. and Kuta, J. (1966) *Principals of polarography*, Academic Press, New York, pp. 531–547]. FIG. 11A shows that a drop in the SPR signal occured at approximately this voltage, as expected. As the Pb metal is oxidized and diffuses away from the surface of the gold, $\lambda_{sp}$ drops from its peak value of 652 nm to 612 nm. During this time, however, $Cu^{2+}$ cations continue to be reduced onto the SPR sensor. This explains why $\lambda_{sp}$ continues to rise even after all of the Pb has been oxidized from the surface, eventually reaching a peak value of 663 nm. The signal would have continued to rise, but at 663 nm the voltage had reached 0.114 V, the Nernst oxidation potential for Cu. This causes the Cu metal to oxidize and diffuse away from the surface of the SPR sensor (Heyrovsky, J. and Kuta, J. (1966) *Principals of polarography*, Academic Press, New York, pp. 531–547). $\lambda_{sp}$ dropped from a value of 663 nm at 703 seconds, reaching the baseline again at 749 seconds. Based on the potentials at which the current peaks occurred, it was possible to identify the different ions in solution. The heights of the current peaks are linearly proportional to the concentration of the ions.

Figure 12A:
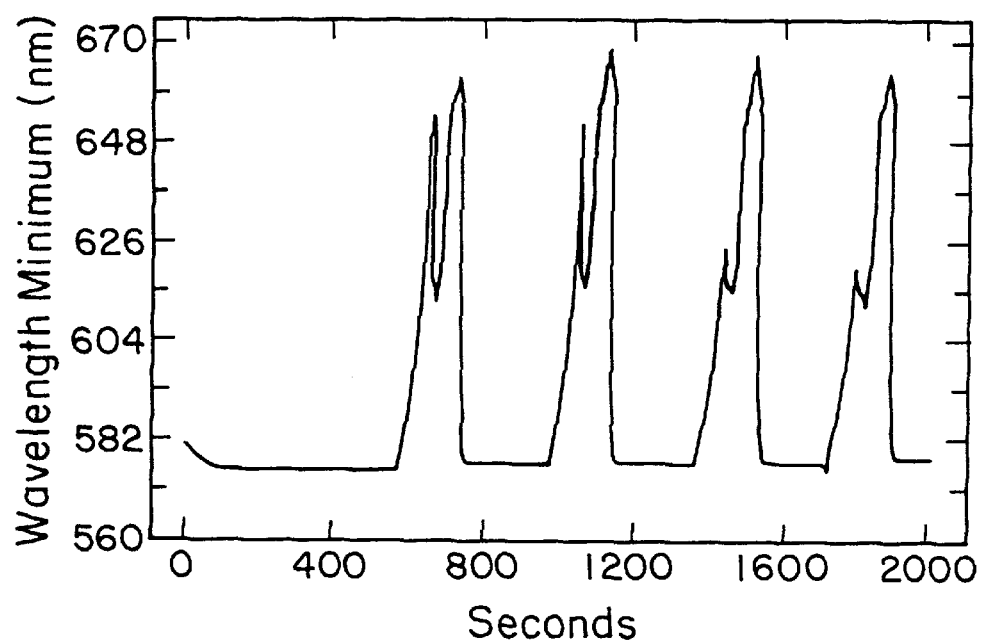
FIG. 12A is a graph of the resonance minimum $\lambda_{sp}$ as a function of time over four consecutive cycles, for the experiment described in FIG. 11A.

The process outlined above was repeated three more times. The SPR signal for all four consecutive runs is shown in FIG. 12A. The Pb peaks were not as pronounced in the last two runs. Without being bound by theory, it is postulated that this may be a result of sensor fouling due to irreversible reactions at the sensor surface, or to an insufficient reduction potential, due to a lack of compensation for the effects of solution resistance.

Figure 12B:
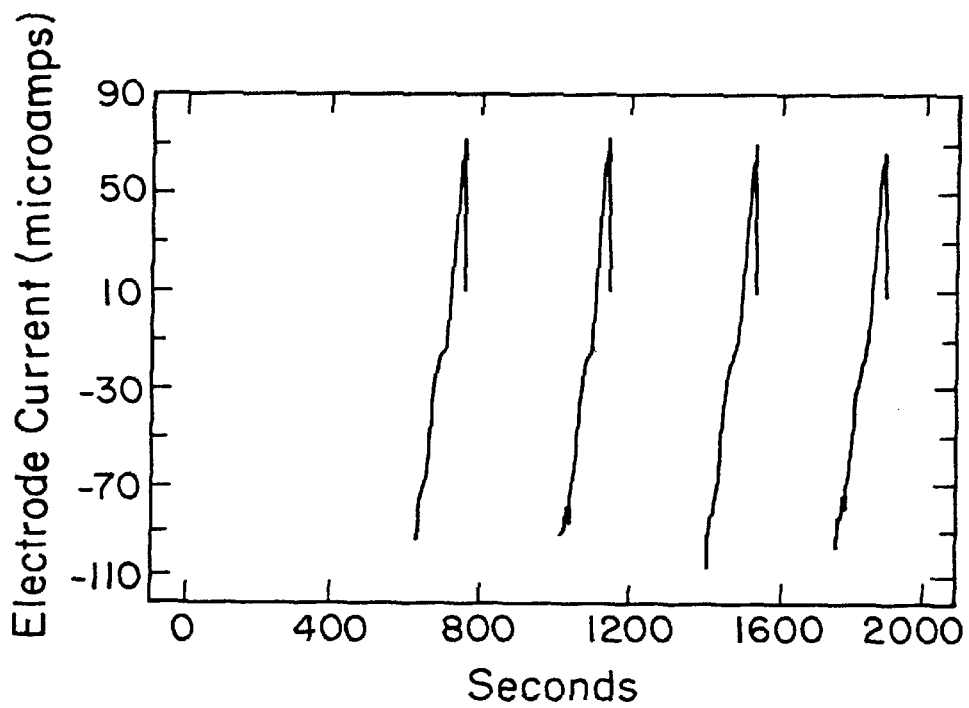
FIG. 12B is a graph of the current flowing through the SPR sensor as a function of time over four consecutive cycles for the experiment described in FIG. 11A.

FIG. 12B shows the current which flowed in the SPR sensor while the voltage was being stepped in the experiment outlined above. Two peaks in the current were predicted: one for Pb at −0.427 V, and one for Cu at 0.114 V. While the Cu peak is clearly present in FIG. 12B, the Pb peak is much less visible. This is probably due to the fact that the SPR electrode has a fairly large surface area (1 cm by $2\pi(200 \mu m)$), which allows a large current to flow. The Pb peak is masked by background currents, due to the effects of solution resistance. Potentiostatic circuitry can be employed to minimize this effect.

Figure 13:
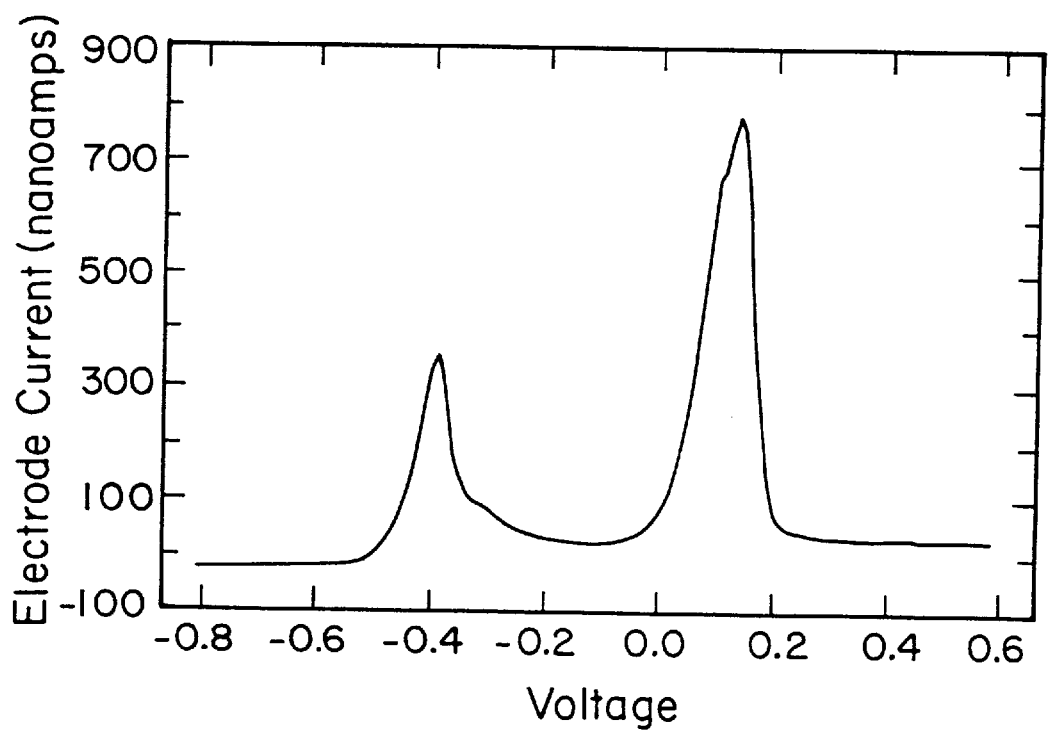
FIG. 13 is a graph of the electrode current for a 24 band gold microelectrode array, as a function of the applied voltage, for a control-type experiment in which standard electrochemical measurements were made on the same solution as was used in the experiment described in FIG. 11A. Twenty-four gold electrodes were used, and the voltage on these electrodes was ramped from −0.8V to 0.6 in increments of 0.01 V every 10 ms.

In order to verify that this was indeed the case, and that we truly were measuring the reduction of both Pb and Cu cations (and the oxidation of the corresponding metals back to their respective cations) with the SPR sensor, a microelectrode array was placed in the beaker. The array was composed of 24 gold electrodes, each having an area of 10 $\mu$m by 0.18 $\mu$m. The voltage on these electrodes was stepped from −0.8 V to 0.6 V in increments of 0.01 V every 10 ms. The current versus voltage plot for this electrode array is shown in FIG. 13; this plot shows that both the Pb and the Cu current peaks are visible at the expected voltages.

The change in the SPR wavelength minimum caused by Pb and Cu ions was approximately 80 nm for concentrations in the parts per million range. Due to the high sensitivity of SPR, it is possible to detect concentrations in the parts per billion range. The method of standard additions can be used to calibrate the sensors of this invention and determine concentrations of analytes.

The current measurements for the SPR sensor weakly detected the Pb cations in the solution. It was shown that this was due to the relatively large area of the SPR electrode. Although any SPR configuration can be used for the device and methods of the present invention, a preferred configuration for an SPR chemical electrode sensor is a miniaturized one. For example, an array of integrated SPR sensors can be used to very accurately detect both SPR and currents signals. The measurement electronics can be incorporated onto the chip, thereby reducing effects of electronic noise.

We claim:

1. A method for performing stripping voltammetry whereby positive ions, negative ions, or redox-active analytes can be detected in a sample, comprising:

(a) contacting the sample with a first sensing area of a surface plasmon resonance sensor;

(b) introducing light into the surface plasmon resonance sensor whereby the light undergoes total internal reflection therein;

(c) either (1) first applying a negative voltage to the first sensing area for a time sufficient so that positive ions or redox-active analytes in the sample are reduced at a surface of the sensing area, after which the voltage is scanned in a positive direction or (2) first applying a positive voltage to the first sensing area for a time sufficient so that negative ions or redox-active analytes in the sample are oxidized at a surface of the sensing area, after which the voltage is scanned in a negative direction; and (d) measuring a surface plasmon resonance signal as a function of voltage applied to the first sensing area.

2. A method according to claim 1 further comprising the step of:

(e) measuring current flow through the sensor as a function of applied voltage.

3. A method according to claim 1 for performing anodic stripping voltammetry to detect analytes in a sample, the method comprising the steps of:

(a) contacting the sample with the first sensing area of the surface plasmon resonance sensor;

(b) introducing light into the surface plasmon resonance sensor whereby the light undergoes total internal reflection therein;

(c) applying a negative voltage to the first sensing area for a time sufficient to allow for an analyte to be reduced at a surface of the first sensing area;

(d) scanning the voltage in a positive direction until the reduced analyte at least begins to be oxidized off the first sensing area; and (e) measuring a surface plasmon resonance signal as a function of voltage applied to the first sensing area.

4. A method according to claim 1 for performing cathodic stripping voltammetry to detect analytes in a sample, the method comprising the steps of:

(a) contacting the sample with the first sensing area of the surface plasmon resonance sensor;

(b) introducing light into the surface plasmon resonance sensor whereby the light undergoes total internal reflection therein;

(c) applying a positive voltage to the first sensing area for a time sufficient to allow for an analyte to be oxidized at a surface of the first sensing area;

(d) scanning the voltage in a negative direction until the oxidized analyte at least begins to be reduced off the first sensing area; and (e) measuring a surface plasmon resonance signal as a function of voltage applied to the first sensing area.

5. A method for detecting redox-active and redox-inactive analytes in a sample, comprising the steps of:

(a) contacting the sample with a first sensing area of a surface plasmon resonance sensor device, said device comprising:
- a surface plasmon resonance sensor comprising an optical fiber having a core and a cladding layer surrounding the core, wherein the optical fiber has a first end and a second end and has a first sensing area located between the first end and the second end or at the second end, wherein the first sensing area is defined by a conducting film in contact with at least a portion of a surface of the core free from the surrounding cladding layer;
- a light source optically coupled to the first end of the sensor such that light propagates by total internal reflection from the first end towards the second end and excites surface plasmon resonance;
- a voltage source electrically coupled to the first sensing area for selectively applying a constant or variable voltage to the first sensing area; and
- a detector for monitoring a surface plasmon resonance signal exiting the surface plasmon resonance sensor as a function of voltage applied to the first sensing area;

(b) introducing light into the surface plasmon resonance sensor whereby the light undergoes total internal reflection therein;

(c) applying a voltage to the first sensing area;

(d) measuring the surface plasmon resonance signal exiting the surface plasmon resonance sensor during or after application of the voltage to detect redox-inactive analytes; and (e) measuring current resulting from application of the voltage or the surface plasmon resonance signal exiting the surface plasmon resonance sensor during or after application of the voltage to detect redox-active analytes.

6. A method for detecting intermetallic compound analytes, in a sample, comprising the steps of:

(a) contacting the sample with a first sensing area of a surface plasmon resonance sensor device, said device comprising:
- a surface plasmon resonance sensor comprising an optical fiber having a core and a cladding layer surrounding the core, wherein the optical fiber has a first end and a second end and has a first sensing area located between the first end and the second end or at the second end, wherein the first sensing area is defined by a conducting film in contact with at least a portion of a surface of the core free from the surrounding cladding layer;
- a light source optically coupled to the first end of the sensor such that light propagates by total internal reflection from the first end towards the second end and excites surface plasmon resonance;
- a voltage source electrically coupled to the first sensing area for selectively applying a constant or variable voltage to the first sensing area; and
- a detector for monitoring a surface plasmon resonance signal exiting the surface plasmon resonance sensor as a function of voltage applied to the first sensing area;

(b) introducing light into the surface plasmon resonance sensor whereby the light undergoes total internal reflection therein;

(c) applying a voltage to the first sensing area; and (d) measuring the surface plasmon resonance signal exiting the surface plasmon resonance sensor during or after application of the voltage to detect intermetallic compound analytes.

* * * * *

UNITED STATES PATENT AND TRADEMARK OFFICE
CERTIFICATE OF CORRECTION

PATENT NO. : 5,858,799

DATED : Jan. 12, 1999

INVENTOR(S) : Yee et al.

It is certified that error appears in the above-identified patent and that said Letters Patent is hereby corrected as shown below:

At column 20, line 29, please replace "(26)" with --(90)--.

Signed and Sealed this

Ninth Day of November, 1999

Attest:

Q. TODD DICKINSON

*Attesting Officer*  *Acting Commissioner of Patents and Trademarks*